US006479146B1

(12) United States Patent
Caruso et al.

(10) Patent No.: US 6,479,146 B1
(45) Date of Patent: Nov. 12, 2002

(54) FABRICATION OF MULTILAYER-COATED PARTICLES AND HOLLOW SHELLS VIA ELECTROSTATIC SELF-ASSEMBLY OF NANOCOMPOSITE MULTILAYERS ON DECOMPOSABLE COLLOIDAL TEMPLATES

(75) Inventors: Frank Caruso; Rachel Anne Caruso, both of Golm; Edwin Donath, Giesenhorst; Helmuth Möhwald, Bingen, all of (DE); Gleb Sukhorukov, Microraion (RU)

(73) Assignee: Max-Planck-Gesellschaft zur Forderung der Wissenschaften, E.V., Munich (DE)

( * ) Notice: Subject to any disclaimer, the term of this patent is extended or adjusted under 35 U.S.C. 154(b) by 0 days.

(21) Appl. No.: 09/646,398

(22) PCT Filed: Mar. 19, 1999

(86) PCT No.: PCT/EP99/01854

§ 371 (c)(1),
(2), (4) Date: Nov. 7, 2000

(87) PCT Pub. No.: WO99/47253

PCT Pub. Date: Sep. 23, 1999

(30) Foreign Application Priority Data

Mar. 19, 1998 (DE) .......................................... 198 12 083
Jul. 15, 1998 (EP) ............................................. 98113181

(51) Int. Cl.[7] ................................................ B32B 5/16
(52) U.S. Cl. ....................... 428/403; 106/409; 428/404; 428/407
(58) Field of Search ............................... 428/403, 404, 428/407; 106/409

(56) References Cited

U.S. PATENT DOCUMENTS

| 3,251,800 A | | 5/1966 | Cooley et al. | |
| 3,855,172 A | | 12/1974 | Iler et al. | |
| 5,344,487 A | * | 9/1994 | Whalen-Shaw | 106/416 |
| 5,487,390 A | | 1/1996 | Cohen et al. | |
| 5,674,519 A | | 10/1997 | Curtis et al. | |
| 6,203,909 B1 | * | 3/2001 | Chassot | 428/403 |

FOREIGN PATENT DOCUMENTS

| EP | 0 415 273 | 3/1991 |
| EP | 0 443 428 | 8/1991 |
| EP | 0 472 990 | 3/1992 |
| EP | 0 667 148 | 8/1995 |
| EP | 0 823 331 | 2/1998 |
| GB | 2 135 954 | 9/1984 |
| WO | 99/47252 | 9/1993 |

OTHER PUBLICATIONS

Nonlinear Hairy Layer Theory of Electrophoretic . . . Latex Particles, Donath, et al., Langmuir, vol. 13, No. 20, (1997) pp. 5294–5305.

* cited by examiner

Primary Examiner—Hoa T. Le
(74) Attorney, Agent, or Firm—Fulbright & Jaworski L.L.P.

(57) ABSTRACT

The invention refers to a new process for preparing coated particles and hollow shells by coating colloidal particles with alternating layers of oppositely charged nanoparticles and polyelectrolytes and optionally removing the colloidal cores.

26 Claims, 20 Drawing Sheets

FABRICATION OF MULTILAYER-COATED PARTICLES AND HOLLOW SHELLS VIA ELECTROSTATIC SELF-ASSEMBLY OF NANOCOMPOSITE MULTILAYERS ON DECOMPOSABLE COLLOIDAL TEMPLATES

SPECIFICATION

The invention refers to a new process for preparing coated capsules and hollow shells by coating colloidal particles with alternating layers of oppositely charged nanoparticles and polyelectrolytes.

The area of thin film fabrication, in which ordered, functional supramolecular structures are the chief goal, has been greatly impacted by the recent introduction of the layer-by-layer (LbL) self-assembly technique (Decher, Science 1997, 277, 1232). The LbL method permits the fabrication of multilayer thin film assemblies on solid supports by the spontaneous sequential adsorption of oppositely charged species from dilute aqueous solutions onto charged substrates. The driving force for the multilayer film build-up is primarily due to the electrostatic attraction and complex formation between the charged species deposited. The LbL approach was initially employed to construct multilayer films of polyelectrolytes (Decher, Science 1997, 277, 1232), and subsequently extended to include proteins (Lvov et al, J. Am. Chem. Soc. 1995, 117, 6117; Onda et al, T. Biotech. Bioeng. 1996, 51, 163; Caruso et al, Langmuir 1997, 13, 3427), nucleic acids (Decher et al, J. Biosens. Bioelectron. 1994, 9, 677; Sukhorukov et al, Thin Solid Films 1996, 284/285, 220; Caruso et al, Anal. Chem. 1997, 69, 2043), dyes (Araki et al, Langmuir 1996, 12, 5393; Yoo et al, Synthetic Metals 1997, 85, 1425; Ariga et al, J. Am. Chem. Soc. 1997, 119, 2224), dendrimers (Tsukruk et al, Langmuir 1997,13, 2171), and various inorganic nanoparticles (Kleinfeld et al, Science 1994, 265, 370; Keller et al, J. Am. Chem. Soc. 1994, 116, 8817; Kotov et al, J. Am. Chem. Soc. 1997, 119, 6821; Kotov et al, J. Phys. Chem. 1995, 99, 13065; Feldheim et al, J. Am. Chem. Soc. 1996, 118, 7640; Schmitt et al, Adv. Mater 1997, 9, 61; Lvov et al, Langmuir 1997, 13, 6195) in polyelectrolyte multilayer assemblies by replacing one of the polyions by a similarly charged species.

The vast majority of studies concerning the LbL technique have employed macroscopically flat charged surfaces as substrates for multilayer film formation. For example, U.S. Pat. No. 5,716,709 describes multilayered nanostructures comprising alternating organic and inorganic ionic layers on a flat substrate, such as a silicon wafer. Recently, Keller et al reported the preparation of alternating composite multilayers of exfoliated zirconium phosphate sheets and charged redox polymers on (3-aminopropyl)-triethoxysilane-modified silica particles (Keller et al, J. Am. Chem. Soc. 1995, 117, 12879).

In more recent studies (Caruso et al, J. Phys. Chem. B. 1998, 102, 2011; Sukhorukov et al., Colloids Surf. A: Physicochem.Eng.Aspects 1998, 137, 253), the LbL approach was successfully applied to utilise submicron- and micron-sized charged colloidal particles as the adsorbing substrates to produce colloid-supported polyelectrolyte multilayer films: regular step-wise polyelectrolyte multilayer growth was observed on the colloids.

Considerable scientific effort has been focussed on the fabrication of composite micro- and nanoparticles that consist of either organic or inorganic cores coated with shells of different chemical composition (Kawahashi and Matijevic, J. Colloid Interface Sci. 1991, 143, 103; Garg and Matijevic, J. Colloid Interface Sci. 1988, 126; Kawahashi and Matijevic, J. Colloid Interface Sci. 1990, 138, 534; Ohmori and Matijevic, J. Colloid Interface Sci. 1992, 150, 594; Giersig et al., Adv. Mater. 1997, 9, 570; Liz-Marzan et al., Langmuir 1996, 12, 4329; Liz-Marzan et al., J. Chem.Soc.Chem.Commun. 1996, 731; Giersig et al., Ber.Bunsenges.Phys.Chem. 1997, 101, 1617; Correa-Duarte et al., Chem.Phys.Lett. 1998, 286, 497; Bamnolker et al., J.Mater.Sci.Lett. 1997, 16, 1412; Margel and Weisel, J.Polym.Sci.Chem.Ed. 1984, 22, 145; Philipse et al., Langmuir 1994, 10, 92). These core-shell particles often exhibit properties which are significantly different to those of the templated core (e.g. different surface chemical composition, increased stability, higher surface area, as well as different magnetic and optical properties), thus making them attractive both from a scientific and technological viewpoint. Applications for such particles are diverse, ranging from capsule agents for drug delivery, catalysis, coatings, composite materials, as well as for protecting sensitive agents such as enzymes and proteins. Previous investigations have demonstrated that polymeric microparticles and inorganic cores can be coated with uniform layers of various materials, including silica, yttrium basic carbonate, zirconium hydrous oxide, either by controlled surface precipitation reactions on the core particles, or by direct surface reactions.

U.S. Pat. No. 5,705,222 discloses a process for preparing composite particle dispersions wherein a plurality of core particles is dispersed in a first solution wherein the core particles do not irreversibly self-flocculate, an amount of polymer is added to the dispersion of core particles, wherein the polymer has an affinity for the dispersed core particles and the excess polymer is removed by a solid/liquid separation process, i.e. centrifugation or decanting.

An important extension of core-shell particles is the subsequent removal of the core, resulting in hollow particles or shells. Removal of the templated core has previously been achieved by calcining the coated particles at elevated temperatures or by chemical reactions causing dissolution of the core material. Hollow, submicron sized shells of yttrium compounds have been produced (Kawahashi and Matijevic, 1991, supra) by coating cationic polystyrene latex with yttrium basic carbonate and subsequently calcining. More recently, silica shells were generated by seeded polymerization of tetraethoxysilane on the surface of polystyrene particles, followed by calcination (Bamnolker et al., 1997, supra). Using a similar method, monodisperse, hollow silica nanoparticles have been produced by silicacoating gold nanoparticles, and by chemically dissolving the cores (Giersig et al., Ber.Bunsenges.Phys.Chem., 1997, supra). Hollow particles represent a special class of materials: their lower density and optical properties make them of interest in the fields of medicine, pharmaceutics, materials science and the paint industry.

Conventional methods for the preparation of coated nanoparticles or hollow nanoshells, however, have several disadvantages, since in many cases the formation of uniform and smooth layer structures having sufficient particle coverage as well as control of thickness is very difficult to achieve.

Further, it was suggested (DE 198 12 083.4) that the use of soluble colloidal cores as templates for the sequential deposition of polyelectrolytes can be used to fabricate novel three-dimensional hollow polymer shells.

Herein we report the construction of composite multilayers of nanoparticles and an oppositely charged polyelectrolyte on submicron-sized colloidal particles via the sequential electrostatic adsorption of nanoparticles and polyelectrolyte from dilute solution. Alternating nanoparticle-polyelectrolyte multilayers with various thicknesses have been fabricated. Further, a novel and yet simple method for the fabrication of submicron-sized, hollow, inorganic or composite organic-inorganic particles via colloid templated electrostatic LBL self-assembly of nanoparticle-polymer multilayers, followed by removal of the templated core and optionally the polymer used in the assembly process is presented.

Thus, a first aspect of the present invention is a process for preparing coated particles comprising the steps:

(a) providing template particles and
(b) coating said template particles with a multilayer comprising (i) alternating layers of oppositely charged nanoparticles and polyelectrolytes and/or (ii) alternating layers of oppositely charged nanoparticles.

Preferably, the template particles have an average diameter of up to 10 µm, more preferably ≦5 µm, and most preferably ≦2 µm. The minimum diameter of the template particles is preferably 10 nm, more preferably 100 nm, and most preferably 200 nm.

Suitable template particles may be selected from organic particles, inorganic particles, or any combination thereof. For example, the template particles may be inorganic particles including inorganic structures. In a preferred embodiment, the template particles are selected from organic polymer latices, such as polystyrene or styrene copolymer latices. On the other hand, also partially cross-linked melamine-formaldehyde template particles can be used which can be disintegrated under mild conditions, e.g. by adjusting the pH value to an acid value of e.g. ≦1.5, by dissolving in mild organic solvents such as DMSO or by chemical reactions, e.g. sulfonation with alkali sulfites, alkali hydrogen sulfites etc. Regarding the preparation of partially cross-linked melamine-formaldehyde template particles reference is made to DE 198 12 083.4, particularly Example 1, where it is described that in the polycondensation of melamine-formaldehyde precondensates (cf. DD 224 602) the polycondensation process can be interrupted after some time, e.g. 1 min to 1 h after start of the reaction, so that dissoluble, partially cross-linked melamine-formaldehyde template particles are obtained.

Other organic template particles, e.g. polystyrene latices, can be disintegrated by dissolving in appropriate organic solvents such as THF or by heating, e.g. to temperatures of 500° C. or greater.

The process according to the present invention comprises coating the template particles with alternating coatings of polyelectrolyte molecules and nanoparticles. The polyelectrolytes are usually polymers having ionically dissociable groups which may be a component or substituent of the polymer chain. Preferably, linear or/and water-soluble polyelectrolytes are used. Depending on the type of dissociable group, polyelectrolytes are subdivided into polyacids and polybases. Upon dissociation polyacids separate protons to give polyanions. Examples of polyacids are polyphosphoric acid, polyvinyl or polystyrene sulphuric acid, polyvinyl or polystyrene sulfonic acid, polyvinyl or polystyrene phosphonic acid and polyacrylic acid. Examples of the respective salts, which are also called polysalts, are polyphosphate, polysulphate, polysulfonate, polyphosphonate and polyacrylate. If the polyelectrolyte is a polycation, the nanoparticles preferably have an overall anionic charge.

Polybases contain groups which are capable of accepting protons, e.g. by reacting with acids to give salts. Examples of polybases are polyamines, such as polyethylene amine, polyvinyl amine and polyvinyl pyridine or poly(ammonium salts), such as poly (diallyl dimethylammonium chloride). Polybases form polycations by accepting protons. Preferably, polybases (i.e. polycations) are used as polyelectrolyte. If the polyelectrolyte is a polyanion, the nanoparticles preferably have an overall cationic charge.

The nanoparticles are preferably inorganic materials and may be selected from ceramic particles, e.g. oxidic ceramic particles, such as silicon dioxide, titanium dioxide, zirconium dioxide optionally doped with other metal oxides, magnetic particles such as iron oxide-containing particles such as $Fe_3O_4$, magneto-optical particles, nitridic ceramic particles, e.g. $Si_3N_4$, carbidic ceramic particles, metallic particles, e.g. gold, silver, palladium and sulfur or selene-containing particles such as cadmium sulfide, cadmium selenide etc. Especially preferred are oxidic ceramic particles such as silicon dioxide. It should be noted, however, that also organic or biological nanoparticles are suitable for performing the present invention, e.g. macromolecules, such as polypeptides, proteins, nucleic acids, etc. Especially preferred biological nanoparticles are proteins, e.g. immunologically reactive proteins such as antigens and antibodies, e.g. IgG, which may be deposited on the template particle alternating with polyelectrolyte molecules. The biological nanoparticles may be deposited as conjugates containing a labelling group, e.g. a fluorescent group such as fluorescein. The resulting particles are suitable for analytical, e.g. immunological, detection methods. Further, an immobilization of enzymes, single enzymes or a plurality of enzymes, e.g. members of an enzymatic cascade, in single layers or different layers is of special interest because of the ability to increase the catalysis efficiency. Substrates could readily diffuse through the film and react with the immobilized enzyme, thereby producing product.

For the preparation of the coated particles according to the present application preferably an aqueous dispersion of template particles of suitable size is provided. The aqueous dispersion may contain a salt, e.g. NaCl in a concentration which preferably ranges from 50 mmole/l to 1 mole/l. Alternating layers of oppositely charged components, i.e. polyelectrolyte molecules and nanoparticles, different types of nanoparticles or combinations thereof are then deposited on said template particles. The pH of the aqueous dispersion is adjusted in such a way that the molecules in each alternating layer, e.g. polyelectrolyte molecules and nanoparticles, each have opposite total charges. The thickness of the coating which is determined by the number of layers is preferably 2 to 1000 nm, with 2 to 40 and particularly 2 to 20, e.g. 3 to 10 coatings being applied. Suitably, each layer may be comprised of a single species of polyelectrolyte or nanoparticle or of a mixture comprising at least two polyelectrolyte or nanoparticle species. Further, for each layer different polyelectrolyte or nanoparticle species may be used.

After application of each layer the excessive molecules (e.g. polyelectrolyte or nanoparticle) which have not contributed to forming the layer are preferably separated off before the next layer is applied. Such separation can be done according to any known method, particularly centrifugation, filtration or/and dialysis.

In a preferred embodiment of the invention the template particles are at first coated with several layers of oppositely charged cationic and anionic polyelectrolytes before the alternating layers of nanoparticles and polyelectrolyte or the alternating nanoparticle layers are applied. The coating of template particles with several layers of oppositely charged polyelectrolytes is described in DE 198 12 083.4 to which express reference is made. Preferably, the template particles are coated with at least two and up to six layers of oppositely charged cationic and anionic polyelectrolytes, e.g. with three layers. The outermost polyelectrolyte layer is preferably oppositely charged with regard to the nanoparticle to be deposited.

The template particles can be of any shape whatsoever, e.g. they can be spherical or rod-shaped. They can have any regular or irregular structure including crystal structures. Furthermore, the template particles can also be composed of several small sub-particles.

The thickness of the shell walls around the template particles can be readily controlled by varying the number of deposition cycles, whilst the shell size and shape are predetermined by the dimensions of the template particle employed. The thickness of the shell can vary in a wide range, e.g. from 2 to 1000 nm, particularly from 5 to 250 nm.

Preferably, the template particles are at least partially disintegrated after the coating has been completed. They can be dissolved in appropriate solvents or thermally (e.g. by calcination to temperatures of at least 500° C.) or—e.g. if partially cross-linked melamine-formaldehyde template particles are used—by mild chemical methods, e.g. in DMSO, or a change in the pH value. After dissolution of the template particles hollow shells remain which are composed of the nanoparticle material and optionally the polyelectrolyte material. The resulting hollow shells may be inorganic or organic shells or composite inorganic-organic or composite inorganic-inorganic shells depending on the method of core removal. For example, when thermal treatment (calcination) is used, all organic matter is removed, hence only inorganic shells are obtained. Exposure to solvent or low-pH solutions to remove the core results in composite hollow particles in which the core is removed but the polyelectrolyte assembled between the nanoparticle layers remains in the shell.

The hollow shells may be characterized by any known methods, e.g. by scanning and transmission electron microscopy and atomic force microscopy. Preferably, the shells are uniform layers of regular thickness and can find applications in numerous areas, such as medicine, pharmaceutics, catalysis, optics, magnetics, separation and sensing methods. In the hollow shells of the present invention active agents, e.g. inorganic or/and organic substances can be encapsulated. Examples of active agents are pharmaceutic agents so that the shells can be used as drug delivery systems in order to transport the active agents to the desired place in the organism. Further, also contrasting agents can be enclosed in the shells, e.g. to improve the quality of images obtained by ultrasonic examination. It is also possible that the hollow shells themselves are used as contrasting agents.

Further possible applications are fillers or pigments in paints, toners in printing or coatings. A still further field of application is the use as high surface area materials for catalysis , e.g. $SiO_2$ or $TiO_2$ shells, for solar energy applications, e.g. $TiO_2$ shells, wherein, if necessary, further active agents may be applied to the inner and/or outer side of the shells. Still another application is the preparation of high-temperature ceramics, e.g. using zirconia nanoparticles or zirconia nanoparticles doped with other metal oxides. Moreover, the nanoparticles can also be used for the slow release of chemical substances, including pesticides, herbicides etc., as magnetic shells, e.g. for medical applications, or for separation and sensing procedures. Finally, the shells may be used as microreactors, e.g. to produce encapsulated colloidal particles, e.g. metal particles such as gold or silver particles, ceramic particles, magnetic particles or semiconductor particles.

Of particular importance for the use of shells is the permeability of the shell wall. The permeability of the shell wall can be influenced by the selection of the polyelectrolytes used for the shell, the wall thickness and the ambient conditions. It is thus possible to selectively determine and change the permeability properties.

The permeability properties can be further modified by pores in at least one of the layers. Such pores can be formed by the polyelectrolytes or nanoparticles themselves if suitably chosen. By incorporating selective transport systems such as carriers or channels into the polyelectrolyte shell the transversal transport properties of the shell can be adapted to the respective application. The pores or channels of the shell wall can be selectively opened and closed, respectively, by chemically modifying and/or changing the ambient conditions. A high salt concentration of the medium used for the deposition of the polyelectrolyte results in a low packing density and a high permeability of the shell wall. On the other hand, a high salt concentration of the medium used for the deposition of the nanoparticles ($SiO_2$) results in a high packing density of the silica particles. Thus, by adjusting the salt concentrations in the deposition medium, the permeability of the shell can be controlled, as desired. Further, the permeability properties of the shell may be modified by selecting the conditions for decomposing the core, e.g. by selecting the temperature and heating conditions in a calcination procedure.

A further aspect of the present invention is a coated particle having a core which is a template particle and a multilayer shell comprising alternating layers of (i) oppositely charged inorganic nanoparticles and polyelectrolytes or (ii) oppositely charged nanoparticles. Preferably, the average diameter of the coated particle is 15 $\mu$m or less, more preferably 100 nm to 1 $\mu$m.

Still a further aspect of the present invention is a hollow shell obtainable by disintegrating the template particles of the coated particle as described above. The hollow shell may be an inorganic structure or a composite organic-inorganic structure depending on the method used to remove the core.

Preferably, the shell contains an active agent which may be selected from pharmaceuticals, contrast agents, herbicides, pesticides, catalysts and pigments.

The shell may be used as a system for slow and/or targeted release of active substances such as pharmaceuticals, herbicides, pesticides etc. Further, the shell may be used for high surface area applications, e.g. as a carrier for catalysts or photovoltaic materials or as a catalyst itself.

It has been demonstrated that the method of the present invention when applied to produce composite nanoparticle-polymer or nanoparticle-nanoparticle multilayers on colloidal template cores, coupled with removal of the core, provides a successful pathway to fabricate novel hollow shells. Important advantages pertaining to this method are: (i) the thickness of the shell walls can be readily controlled by varying the number of deposition cycles; (ii) the shell size and shape are predetermined by the dimensions of the templating colloid employed; (iii) the method is generally applicable to a wide variety of charged nanoparticles, thereby making possible the production of various inorganic, composite-inorganic (e.g. magnetic nanoparticle and $SiO_2$ or $TiO_2$) and composite inorganic-organic shell structures by the simple solution adsorption of charged particles in alteration with polymer; (iv) the method is a suitable alternative of those currently used (e.g. surface precipitation reactions) to produce hollow shells, with the added advantage of eliminating the necessity of more complex preparation procedures; and (v) it can be applied to systems for which the current methods are not suitable.

Further, the invention is illustrated by the following figures and examples:

FIG. 1 is a schematic illustration of the assembly of composite multilayers on colloid latices and the subsequent colloid and polyelectrolyte (optional) removal, resulting in hollow inorganic or composite shells. The first stage involves the sequential adsorption of oppositely charged polyelectrolytes, e.g. a $Pr_3$ coating [poly (diallyldimethylammonium chloride) (PDADMAC)/poly (styrene sulfonate), sodium salt (PSS)/PDADMAC] (step 1) in order to produce a smooth and uniformly positively charged outer surface to facilitate the adsorption of negatively charged $SiO_2$ nanoparticles. Subsequent alternate adsorption of $SiO_2$ (step 2) and PDADMAC (step 3) results in $SiO_2$-PDADMAC multilayers being formed on the latices. The latices may be decomposed by calcination or exposure to low pH or solvent, whereby hollow inorganic or composite inorganic-organic shells are obtained.

FIG. 2 is a normalized light scattering intensity distribution of $Pr_3$-coated PS latices (squares) and PS latices coated with $Pr_3/(SiO_2/PDADMAC)_N$ wherein N=1 (circles), N=2 (triangles) and N=4 (diamonds). Multilayer growth is confirmed by the systematic shift in the SPLS intensity distributions.

FIG. 3 are transmission electron micrographs (TEM) of uncoated PS latices (a) and PS latices coated with $Pr_3/(SiO_2/PDADMAC)_N$ wherein N=1 (b), N=2 (c) and N=4 (d). Regular growth of the $SiO_2$-PDADMAC multilayers is seen by an increase in diameter of the coated PS latices. The scale bar corresponds to all four TEM images shown.

FIG. 4 shows scanning electron micrographs (SEM) of PS latices coated with one $SiO_2$/PDADMAC multilayer (a) before and (b) after calcination. Uniform and smooth multilayer coatings are apparent in (a). The calcination process results in the PS latex core being removed (b): the thickness of the shell wall with one $SiO_2$ layer is not always sufficient to maintain the original sphericity of the PS latices (breakage of the hollow shells could also be caused by the vacuum in the SEM). Some intact shells were also observed with one $SiO_2$ layer.

FIG. 5 shows SEM micrographs of PS latices coated with three $SiO_2$/PDADMAC multilayers (a) before and (b) after calcination. Homogenous coatings are produced on the PS latices (a). Both complete, intact and broken shells are seen in (b): intact spheres are observed for the calcined sample with 3 $SiO_2$ layers; some of the shells are broken as a result of applying a force to them. The thickness of the silica wall is also significantly increased from that shown in FIG. 4 (image a) as a result of successive $SiO_2$/PDADMAC depositions.

Figure 12:
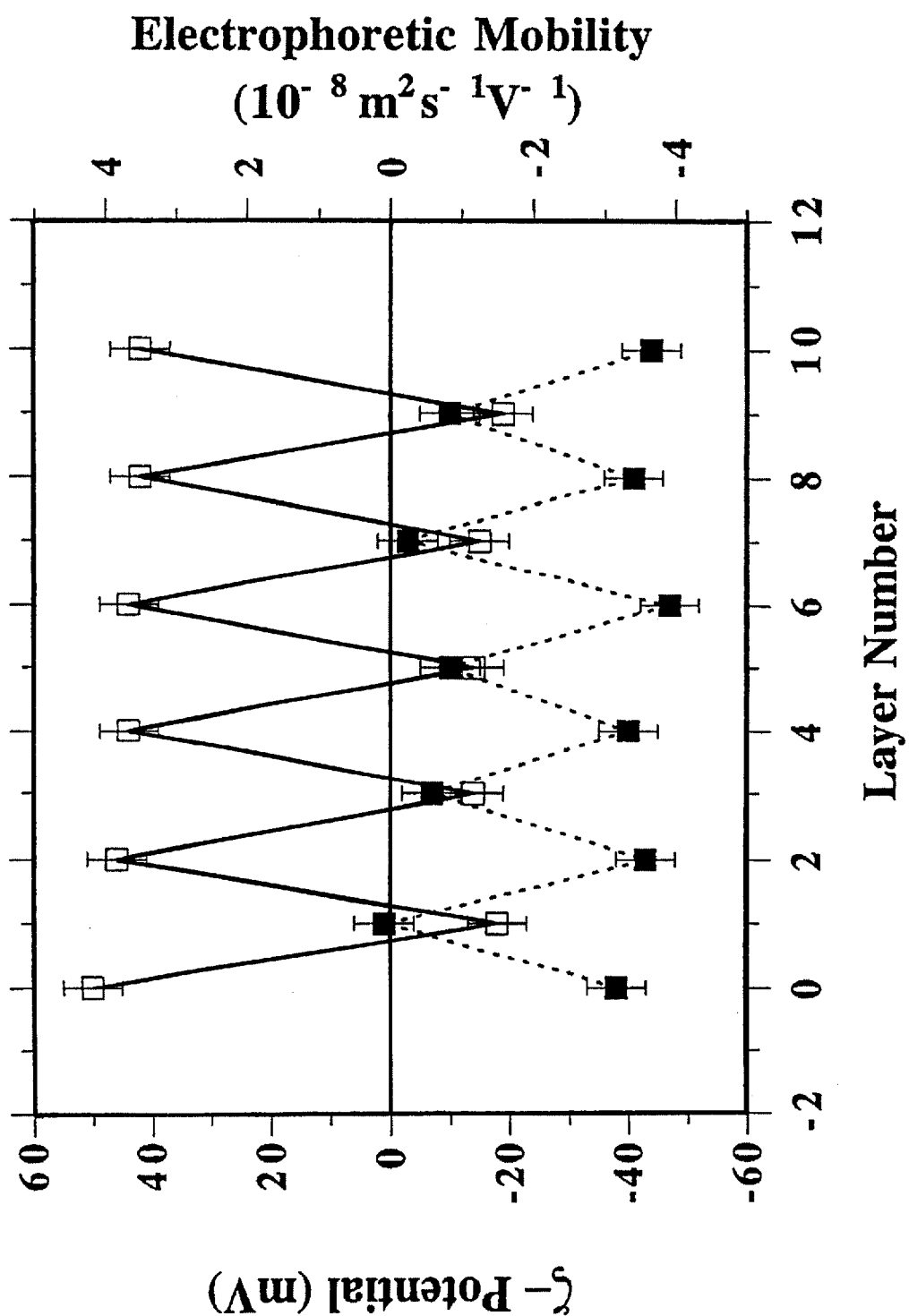

FIG. 12 shows the relationship of Zeta-potential and electrophoretic mobility as a function of polyelectrolyte layer number for FITC-BSA/PDADMAC (open squares) and IgG/PSS (filled squares) multilayers on polyelectrolyte-modified PS latex particles. FITC-BSA multilayers were formed on PDADMAC/PSS/PDADMAC-coated PS latex particles and IgG multilayers on $(PAH/PSS)_2$-coated particles. The odd layer numbers correspond to protein adsorption and the even layer numbers to polyelectrolyte deposition.

Figure 13:
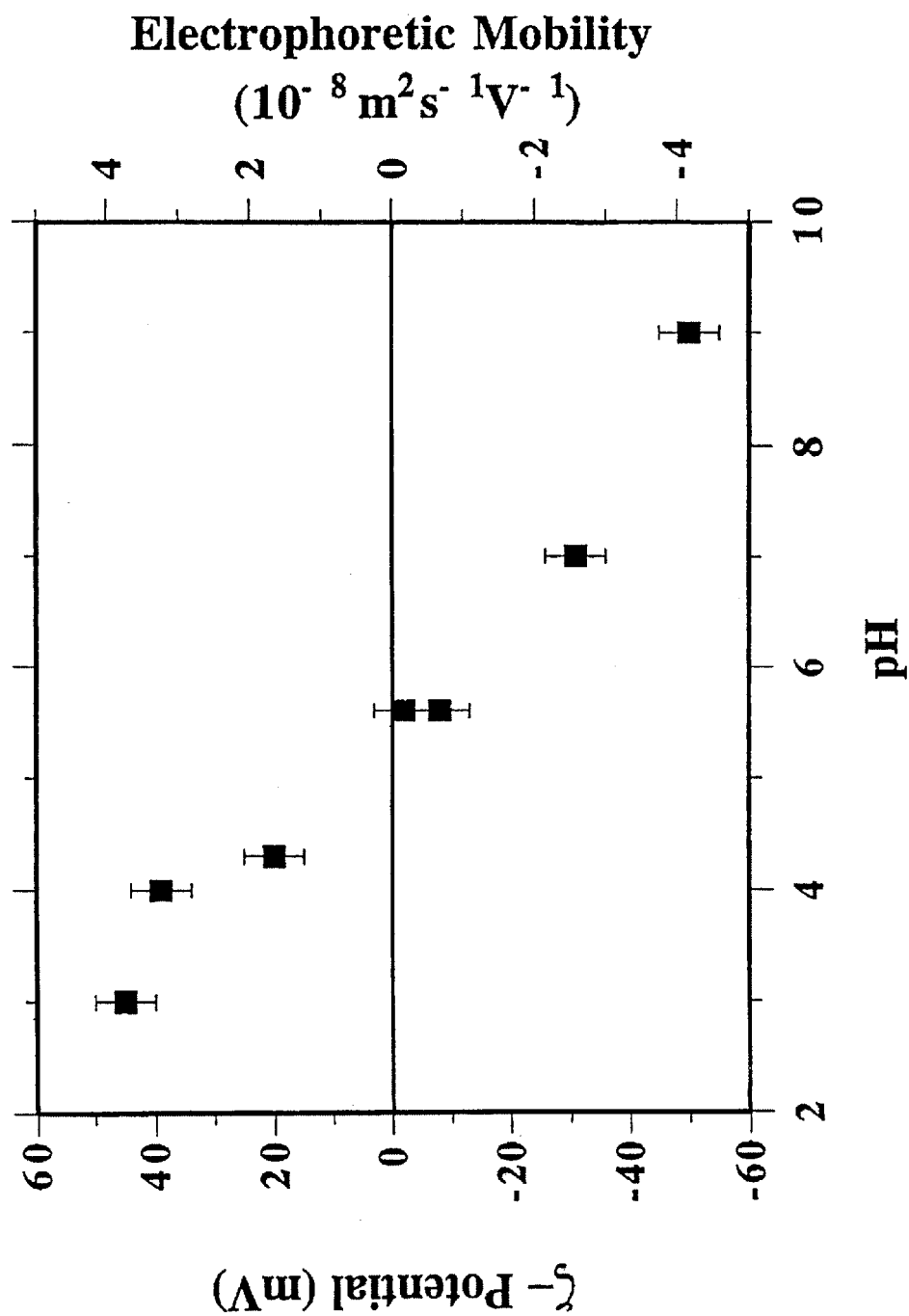

FIG. 13 shows Zeta-potential and electrophoretic mobility as a function of pH for a monomolecular IgG layer adsorbed on $(PAH/PSS)_2$coated PS latex particles.

Figure 14:
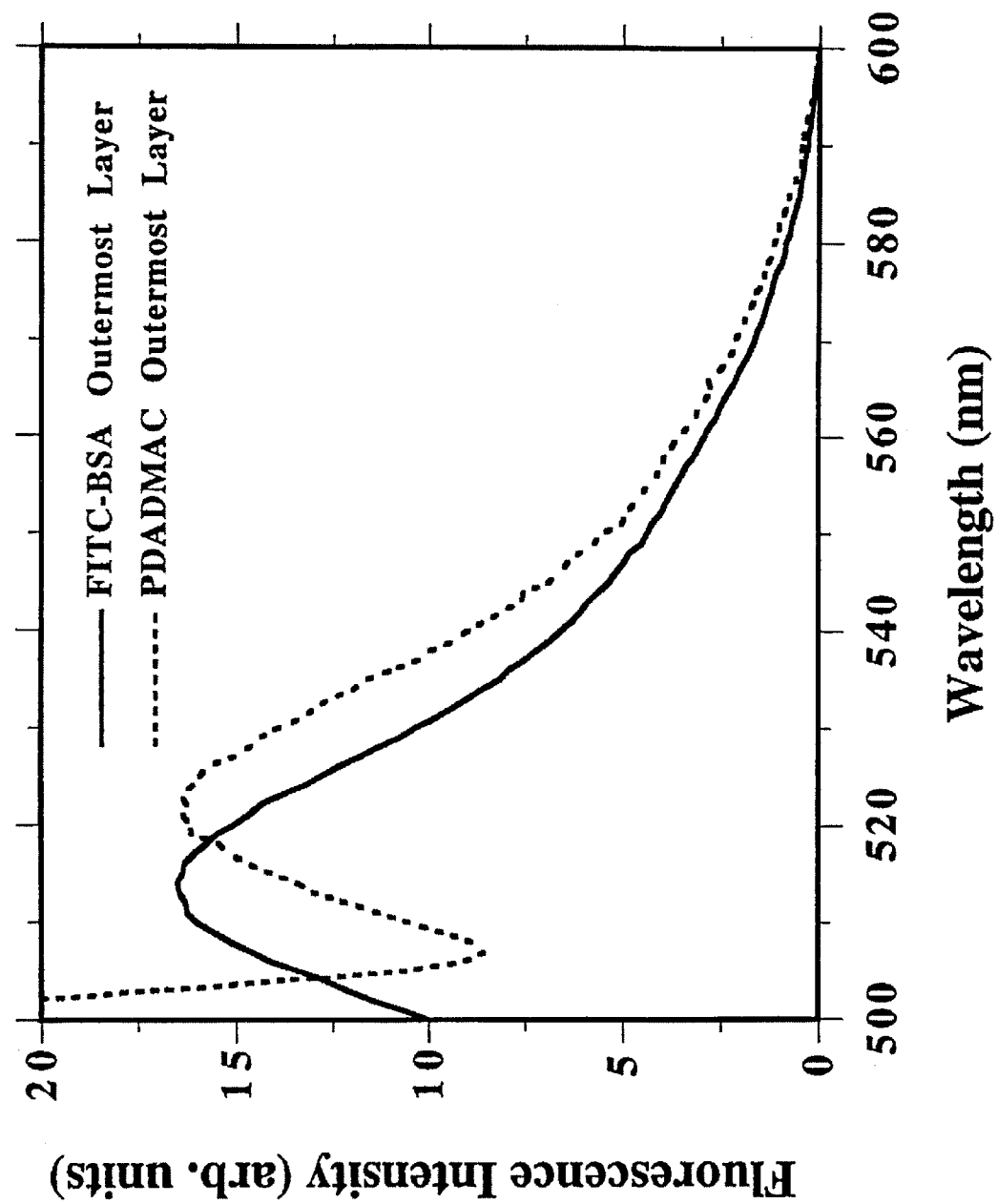

FIG. 14 shows fluorescence spectra of FITC-BSA in multilayer films of FITC-BSA/PDADMAC assembled onto PDADMAC/PSS/PDADMAC-precoated PS latex particles. The solid line corresponds to the spectrum of the multilayer film when FITC-BSA forms the outer layer, and the dashed line to that of the same film with PDADMAC deposited on top.

Figure 15:
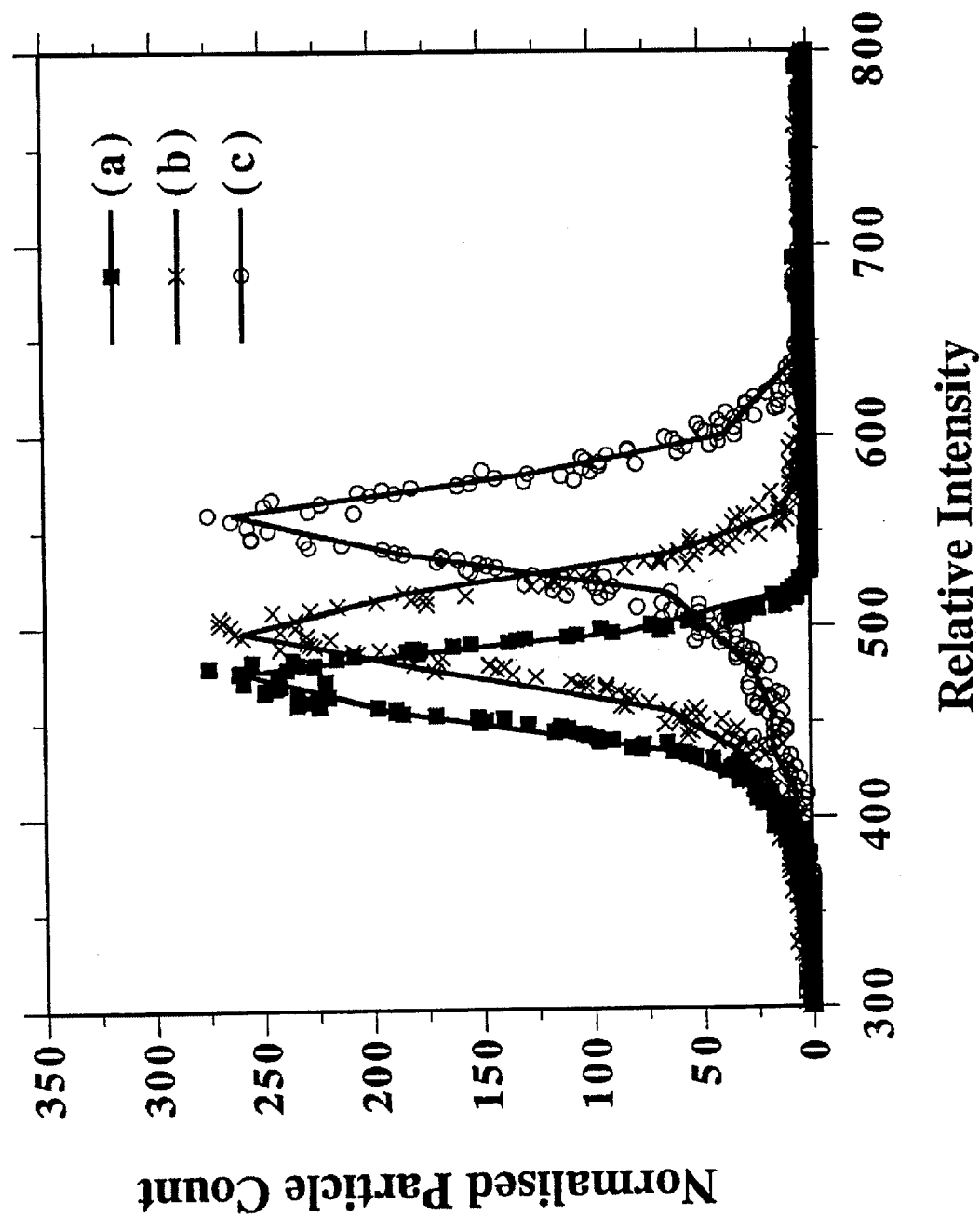

FIG. 15 shows normalised single particle light scattering (SLPS) intensity distributions of PDADMAC/PSS/PDADMAC-coated PS latex particles (a) and the same particles with one (b) and (c) three multilayers of FITC-BSA/PDADMAC. The final multilayer film structures on the colloids are: [PDADMAC/PSS/PDADMAC/(FITC-BSA/PDADMAC)$_N$] wherein (a) N=0, (b) N=1, and (c) N=3.

Figure 16:
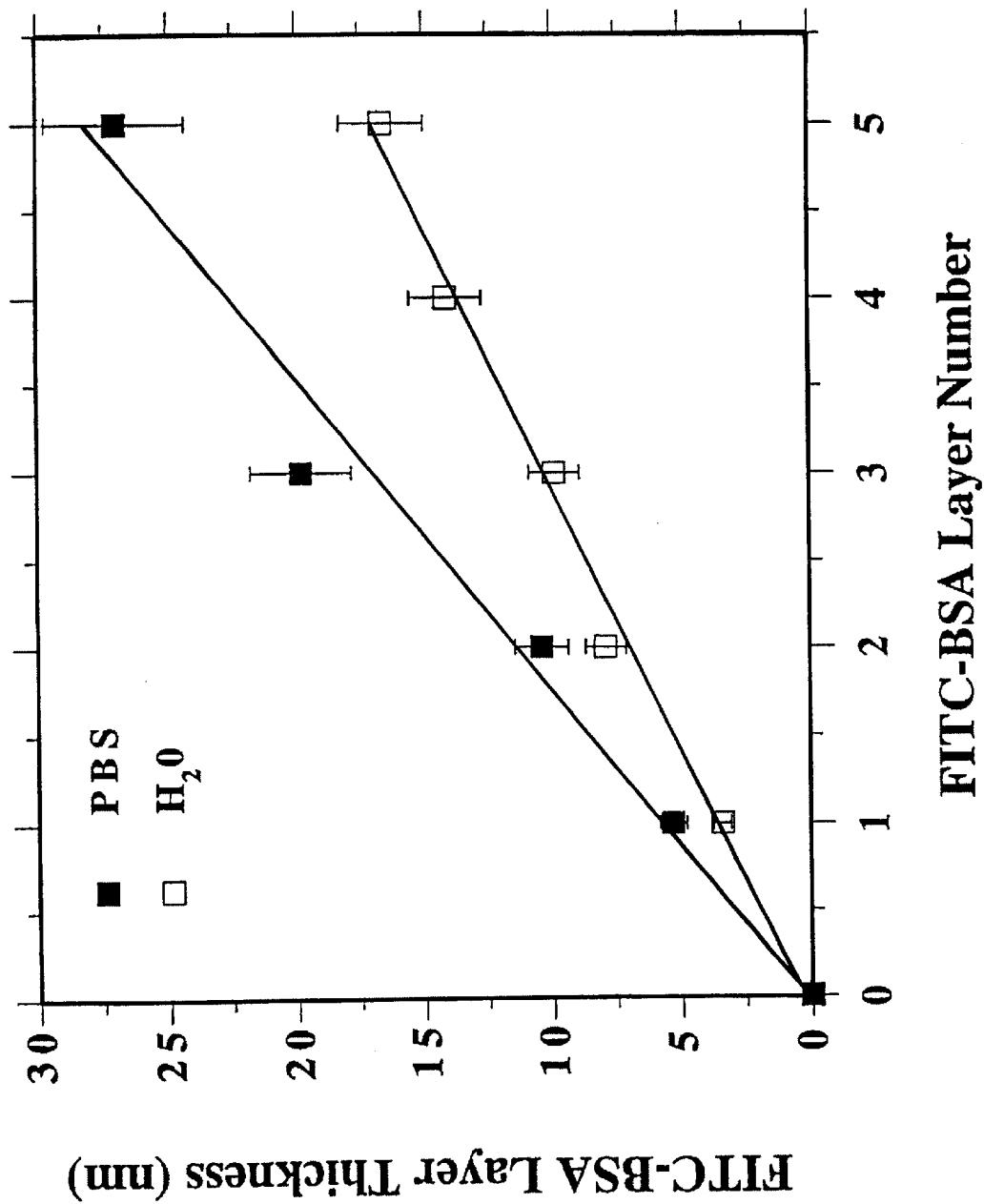

FIG. 16 shows FITC-BSA layer thickness (determined from SPLS) as function of protein layer number for FITC-BSA multilayers assembled on PDADMAC/PSS/PDADMAC-coated PS latex particles. The FITC-BSA multilayers were deposited in alternation with PDADMAC.

Figure 17:
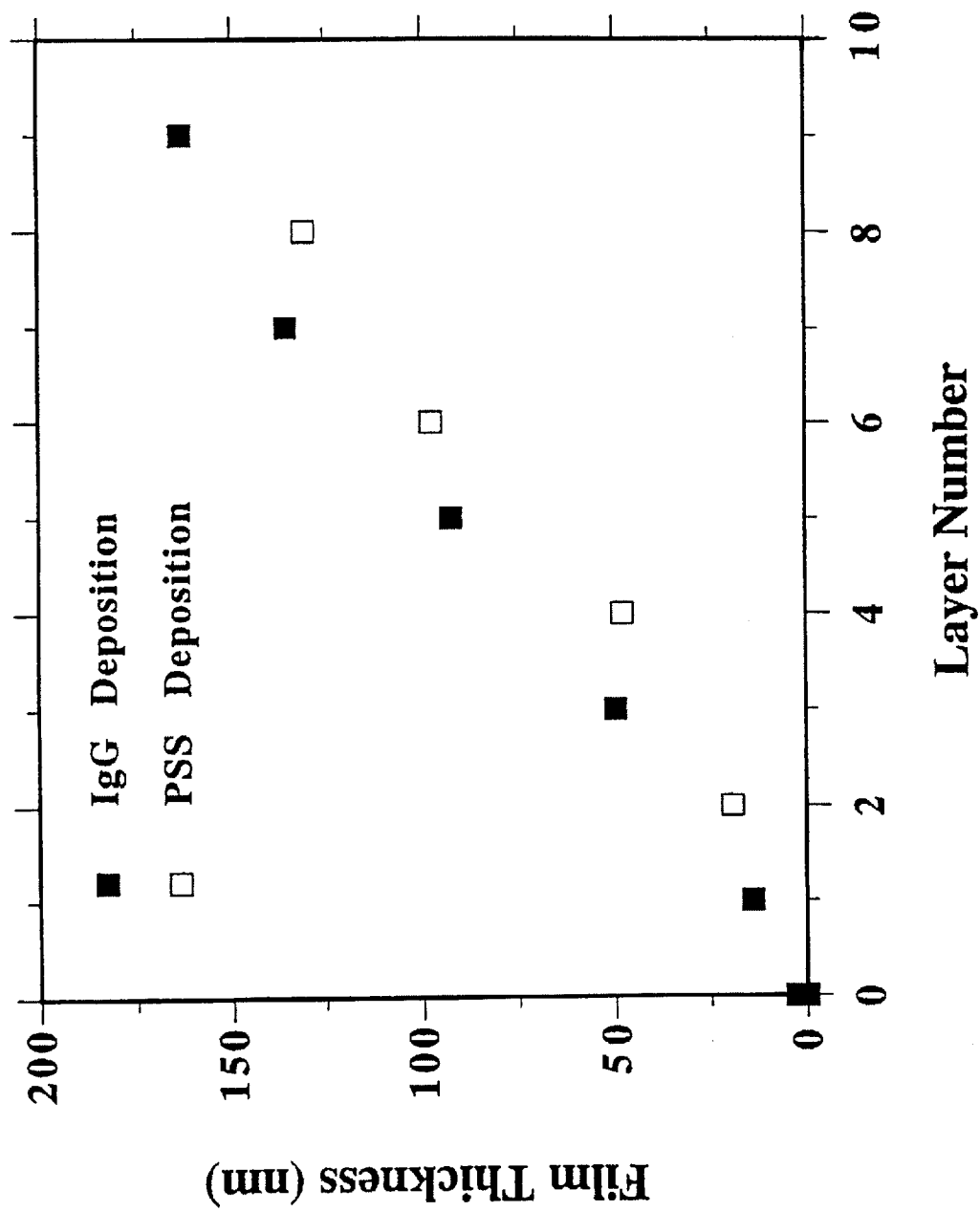

FIG. 17 shows the total film thickness (determined from SPLS) as a function of layer numbers for IgG/PSS multilayers assembled onto $(PAH/PSS)_2$-coated PS latex particles. The odd and even layer numbers correspond to protein and polyelectrolyte deposition, respectively.

Figure 18:
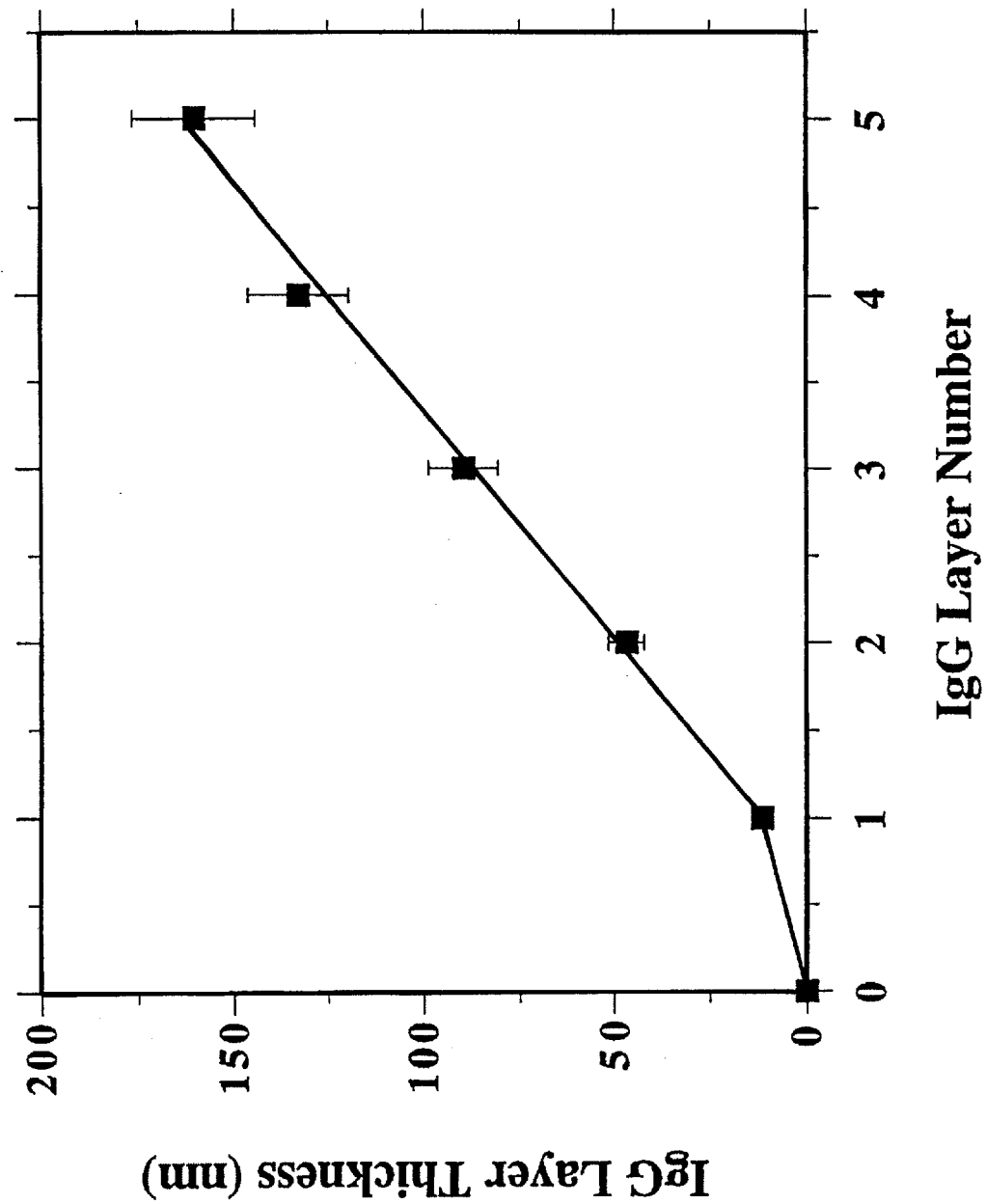

FIG. 18 shows IgG layer thickness (determined from SPLS) as a function of protein layer number for IgG multilayers deposited in alternation with PSS on $(PAH/PSS)_2$-coated PS latex particles.

Figure 19:
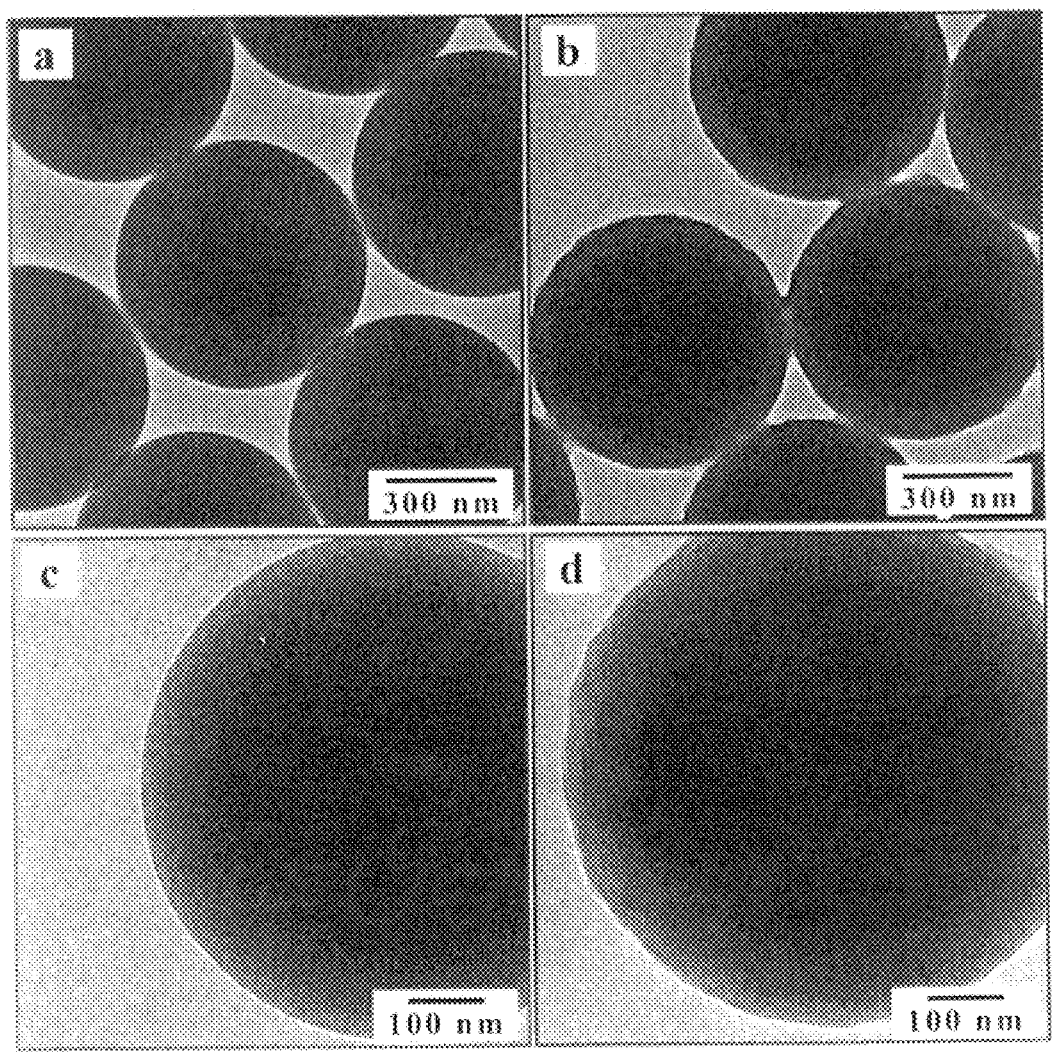

FIG. 19 shows TEM micrographs of PDADMAC/PSS/PDADMAC-coated PS latex particles (a and c) and the same particles additionally coated with [(FITC-BSA/PDADMAC)$_2$/FITC-BSA] (b and d).

Figure 20:
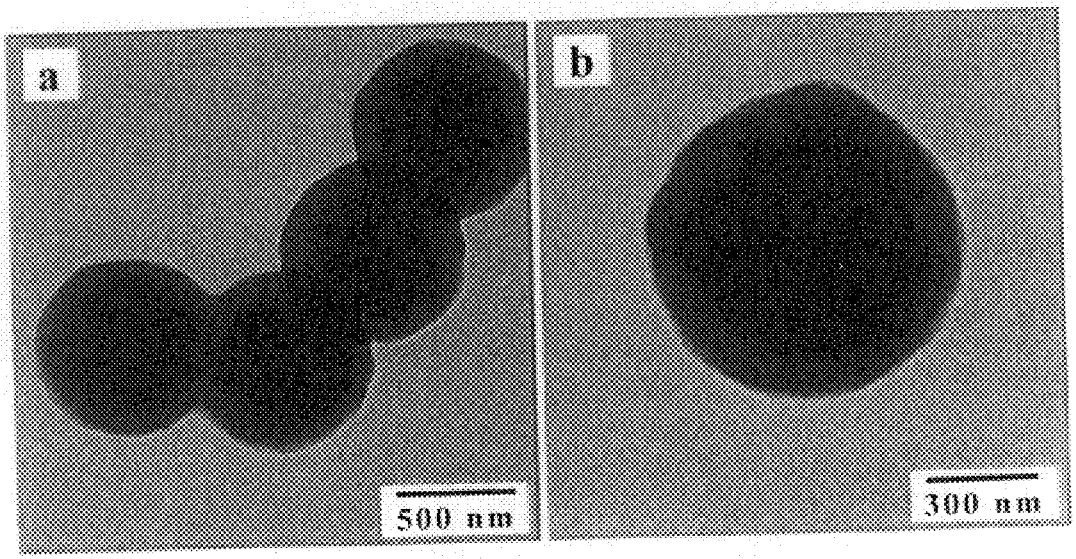

FIG. 20 shows TEM micrographs of IgG multilayers assembled onto $(PAH/PSS)_2$-coated PS latex particles. The final multilayer film structure on the particles is $[(PAH/PSS)_2/(IgG/PSS)_2/IgG]$. Image (b) is at a higher magnification than (a).

EXAMPLE 1

Alternating $SiO_2$-poly(diallyldimethylammonium chloride) (PDADMAC) multilayers were prepared by first assembling a precursor three-layer PDADMAC and poly (styrene sulfonate) sodium salt (PSS) film ($Pr_3$) onto negatively charged 640 nm diameter polystyrene (PS) latices and then $SiO_2$-PDADMAC multilayers on the $Pr_3$-coated PS latices.

The $Pr_3$ film (PDADMAC/PSS/PDADMAC) was formed by the alternate adsorption of PDADMAC (Aldrich, $M_w$<200,000) and PSS (Aldrich, $M_w$ 70,000) from aqueous solutions: 0.5 mL of 1 mg mL$^{-1}$ aqueous polyelectrolyte solution (containing 0.5 M NaCl) was added to the PS latices ($10^{10}$ particles in 0.5 mL $H_2O$), 20 min allowed for adsorption, and excess polyelectrolyte removed by 4 repeated centrifugation (13500×g) /wash/redispersion cycles. (SPLS measurements reveal that about 0.5% of the PS particles are lost at each wash/centrifugation/redispersion step). The $Pr_3$-coated PS latices exhibit a positive surface charge, as determined from electrophoretic mobility (EPM) measurements. Negatively charged sulfate-stabilized PS latices were prepared as described in Furusawa et al, Kolloid-Z. u. Z. Polymere 1972, 250, 908.

$SiO_2$-PDADMAC multilayers on the PS latices were formed by adding 50 μL of an aqueous 40 wt % $SiO_2$ suspension (Ludox TM, DuPont) to the $Pr_3$coated PS latices dispersed in 0.1 M NaCl (larger amounts of $SiO_2$ adsorb when the adsorbing solution contains NaCl), allowing 15 min for $SiO_2$ adsorption, removing excess $SiO_2$ by 4 repeated centrifugation (13500×g)/wash/redispersion cycles, and subsequently depositing PDADMAC (1 mg $mL^{-1}$/0.5 M NaCl). The isoelectric point of the $SiO_2$ particles is 3, therefore $SiO_2$ is negatively charged under the conditions of adsorption (pH 5–6).

Electrophoretic mobility (EPM) measurements using a Malvern Zetasizer 4 show that the surface charge of the multilayer-coated particles alternates from negative to positive with each adsorption of $SiO_2$ and PDADMAC, respectively. This qualitatively demonstrates that the composite $SiO_2$-PDADMAC multilayers are formed by the step-wise adsorption of $SiO_2$ and PDADMAC.

Figure 1:
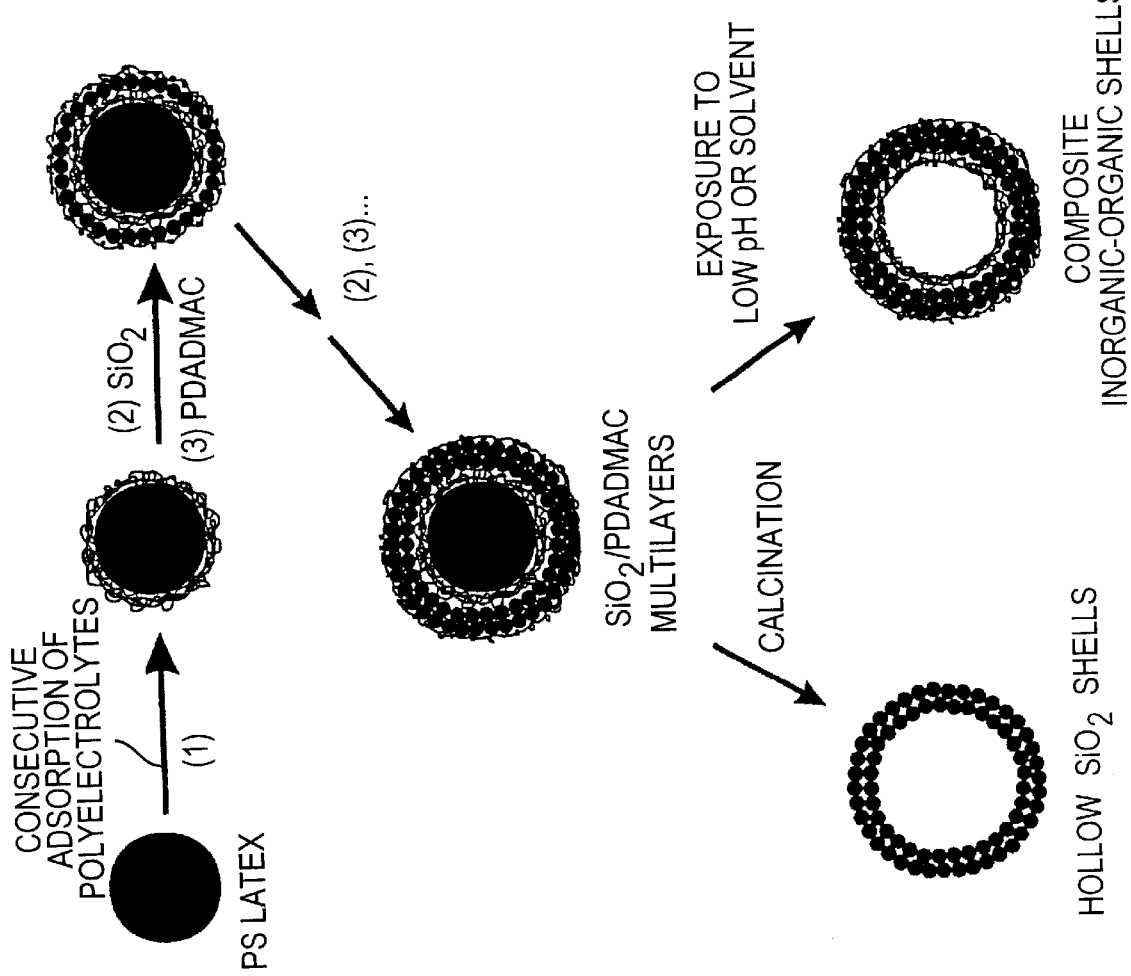
Figure 2:
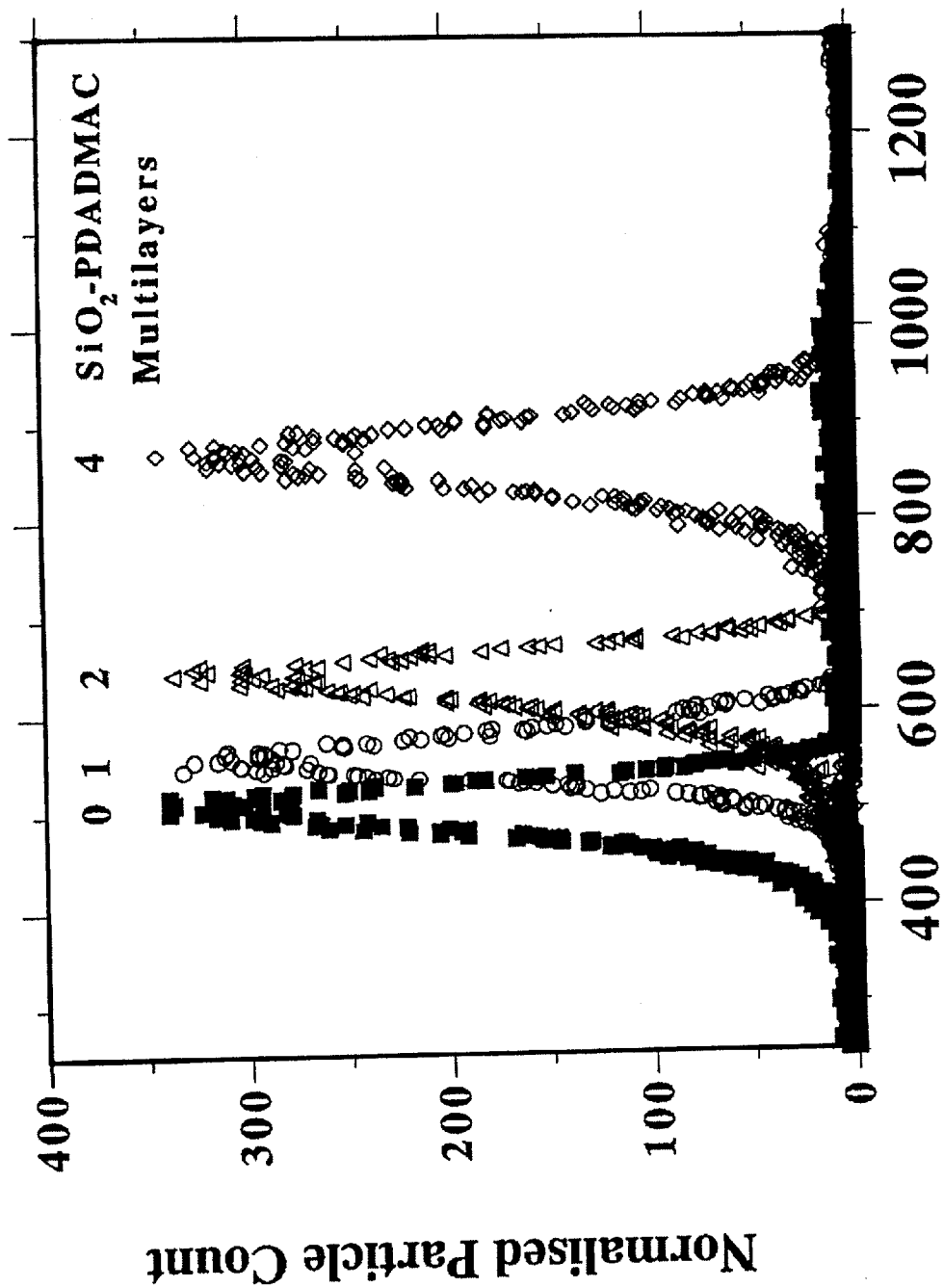

The growth of the $SiO_2$-PDADMAC multilayers on the PS latices was first followed by the method of single particle light scattering (SPLS) (Lichtenfeld et al, Progr. Colloid Polym. Sci. 1997, 104, 148). Normalised SPLS intensity distributions for the $Pr_3$-coated PS latices and those coated with 1, 2 and 4 $SiO_2$-PDADMAC multilayers are shown in FIG. 2. Deposition of the $SiO_2$-PDADMAC multilayers onto the PS latices is manifested as a shift (in the x-axis direction) in the SPLS intensity distributions, confirming multilayer growth. Using the SPLS technique, it is also possible to distinguish between singlets, doublets and triplets (Lichtenfeld et al, Progr. Colloid Polym. Sci. 1997, 104, 148): no aggregation of the multilayer-coated particles is observed, as no intensity peaks are observed at higher intensities.

Using the Raleigh-Debye-Gans theory (Kerker, The Scattering of Light and Other Electromagnetic Radiation: Academic Press: New York, London, 1969) and an estimated refractive index (n) of 1.40 for the adsorbed layer(s), the average thickness calculated for each $SiO_2$-PDADMAC layer pair for $PS/Pr_3/(SiO_2/PDADMAC)_N$ multilayers with N=1–5 is 30±6 nm. This value closely corresponds to the mean diameter of $SiO_2$ particles (26±4 nm, determined from TEM), and suggests that on the average approximately a monolayer of $SiO_2$ is deposited with each $SiO_2$ adsorption. The layer thickness increases linearly with the number of $SiO_2$ or $SiO_2$-PDADMAC layers deposited onto the PS latices.

Figure 3:
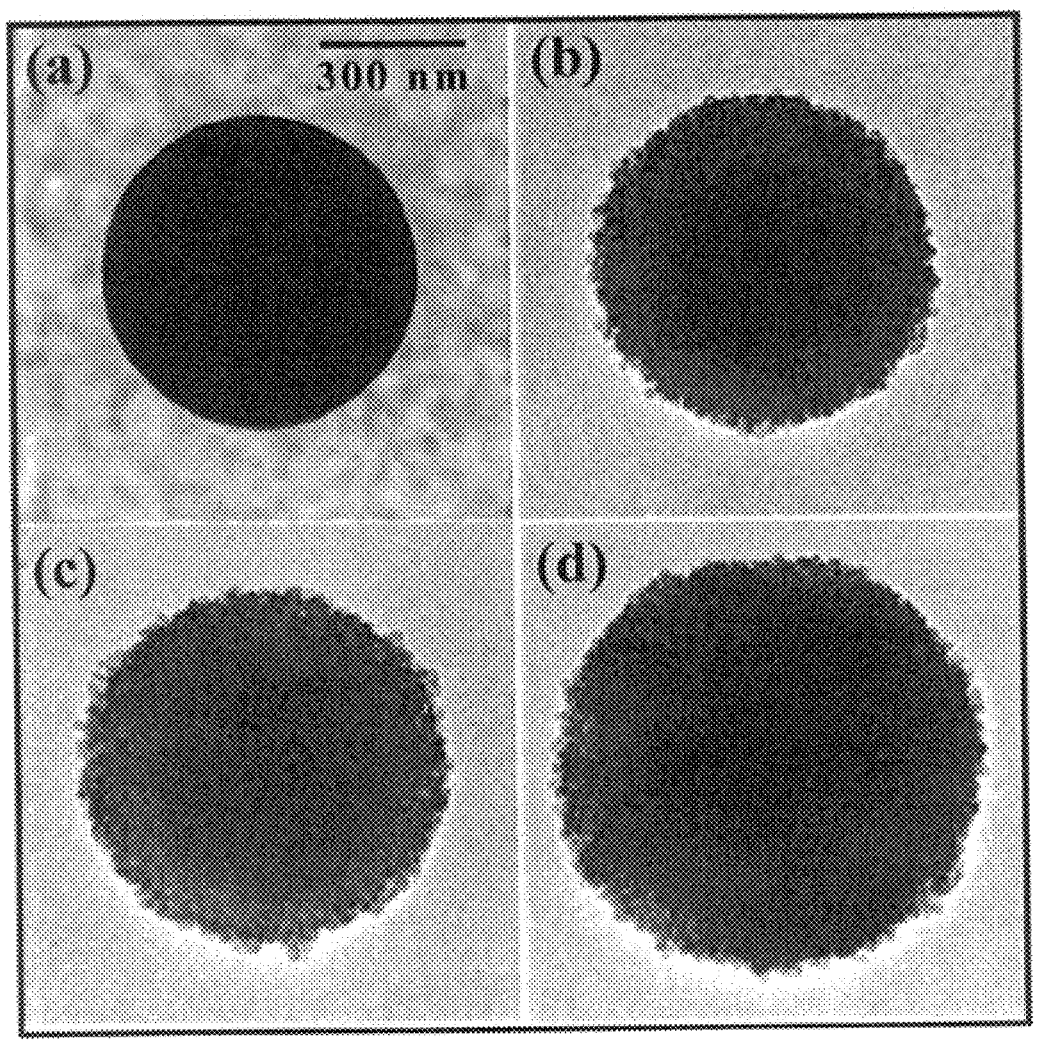

Direct observation of the multilayer growth process was provided by transmission electron microscopy (TEM) using a Philips CM12 microscope operating at 120 kV: representative TEM images of uncoated PS latices and $Pr_3$-modified PS latices coated with $SiO_2$-PDADMAC multilayers are displayed in FIG. 3. The uncoated PS latices (a) exhibit a smooth surface. TEM images obtained for PS latices coated with $Pr_3$ are essentially identical to those of the uncoated PS latices: the thickness increase (ca. 4 nm, determined from SPLS experiments) is not discernible. The presence of $SiO_2$-PDADMAC multilayers on the PS latices results in both an increase in surface roughness and an increase in the diameter of the PS latices (b–d). The increase in surface roughness is due to adsorbed $SiO_2$. It was found that adsorption of PDADMAC onto an outermost layer of $SiO_2$ reduces the surface roughness of the multilayer. This finding is corroborated by preliminary scanning electron microscopy (SEM) measurements.

The increase in diameter with increasing $SiO_2$-PDADMAC multilayer number of the coated PS latices (relative to uncoated PS latices, a) is approximately 60 nm (b), 140 nm (c) and 250 nm (d), for 1, 2 and 4 $SiO_2$-PDADMAC multilayers, respectively. Evaluation of the TEM data for $PS/Pr_3/(SiO_2/PDADMAC)_N$ multilayers with N=1–5 yields an average diameter increment of 65±5 nm, corresponding to a layer thickness of ca. 32 nm, for the $SiO_2$-PDADMAC layer pair.

To remove the PS latex the solution was initially dried at room temperature and then placed into an oven under $N_2$ and heated to 500° C. at a rate of 5 K/min. After 4 h at this temperature the gas was changed to $O_2$ and the sample remained at 500° C. for another 8 h. The sample was then cooled to room temperature under $O_2$. The samples were then examined by SEM using a Zeiss DSM instrument operated at an accelerating voltage of 20 kV.

Figure 4:
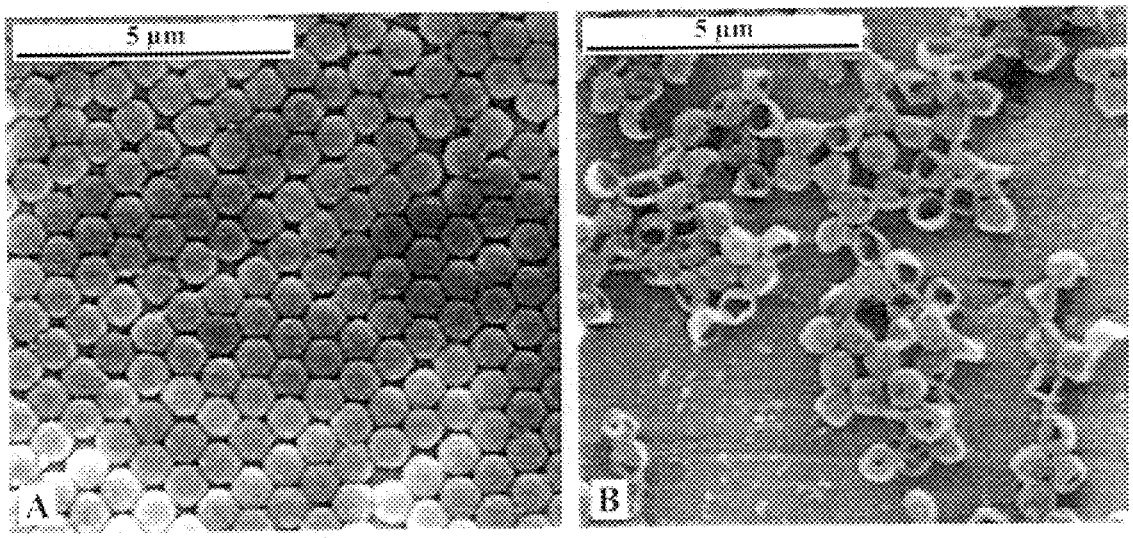
Figure 5:
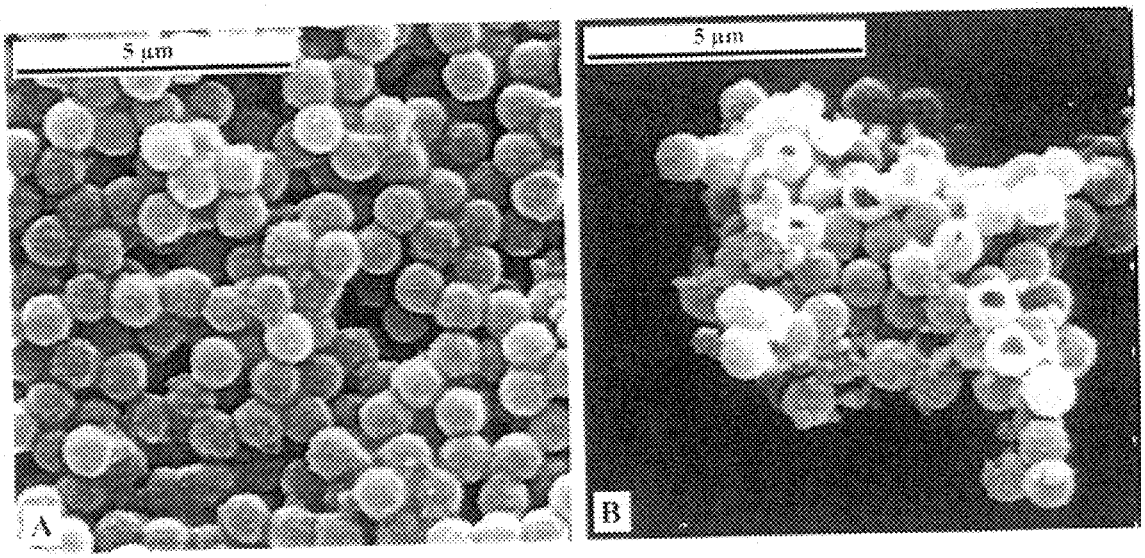
Figure 6:
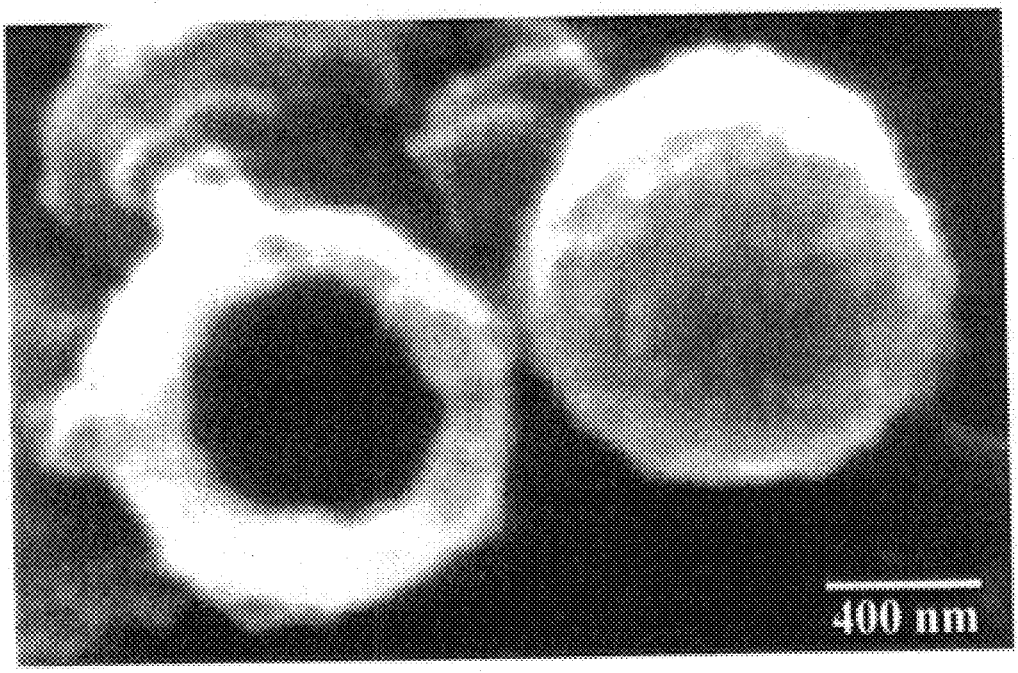
FIG. 6 is a higher magnification of FIG. 5b.
Figure 7:
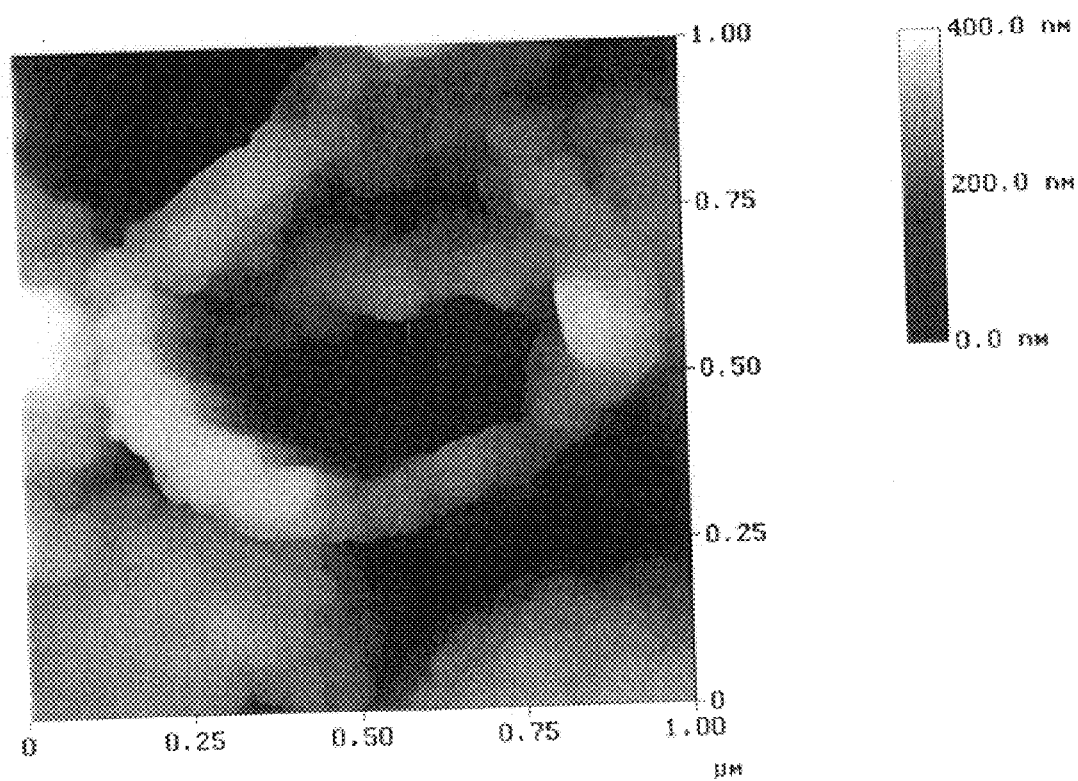
FIG. 7 is an atomic force (AFM) image of a broken sphere wall.
Figure 8:
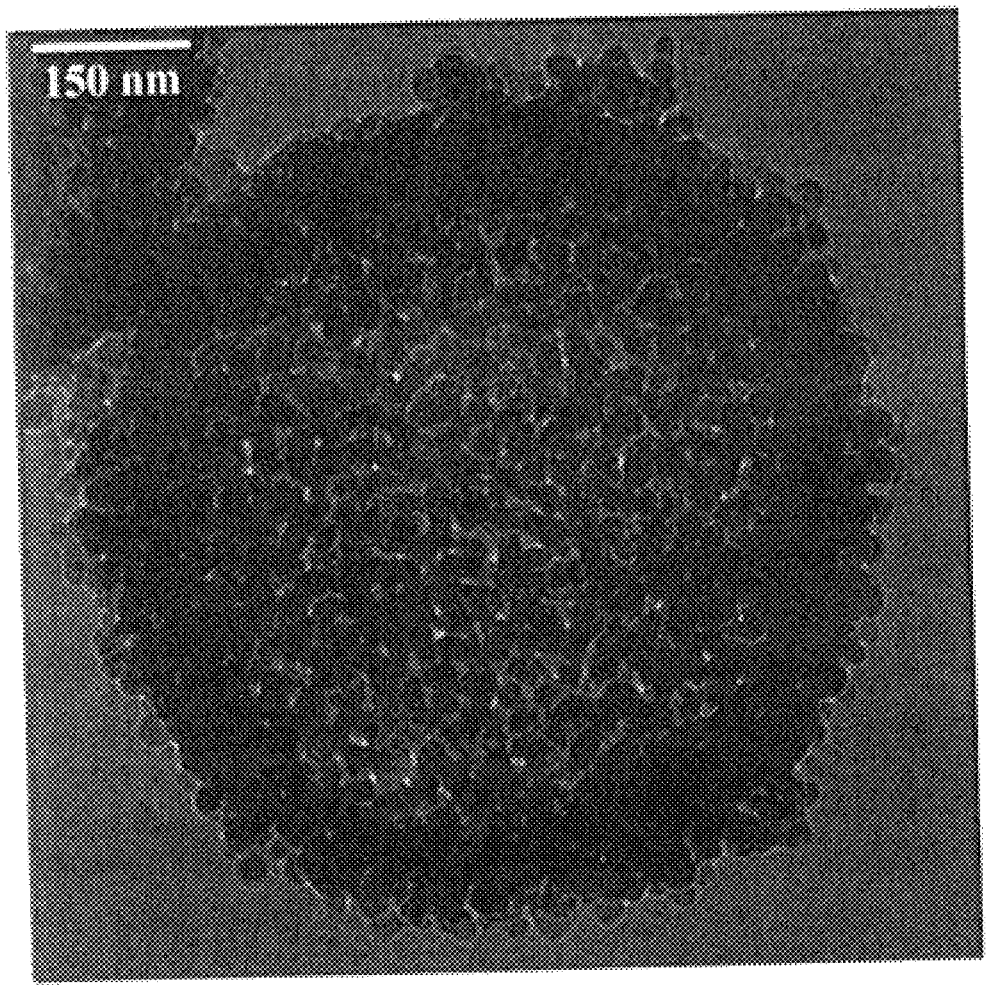
FIG. 8 shows a TEM micrograph of hollow silica spheres produced by calcination of PS latices coated with two $SiO_2$/PDADMAC multilayers.
Figure 9:
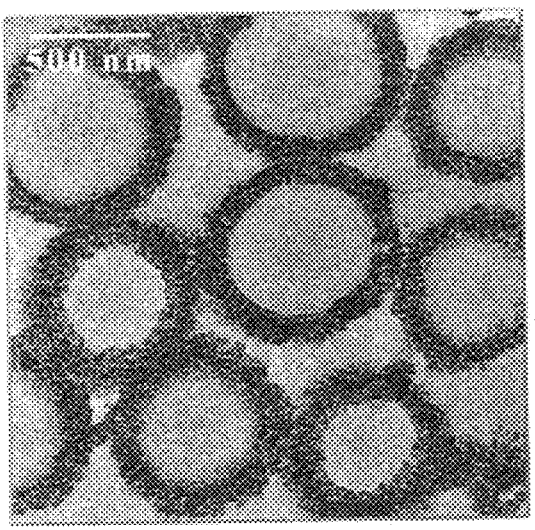
FIG. 9 shows a TEM micrograph of a cross section of silica hollow capsules obtained after calcination of PS latices coated with three $SiO_2$/PDADMAC multilayers. The calcined samples were embedded in a resin prior to imaging.
Figure 9:
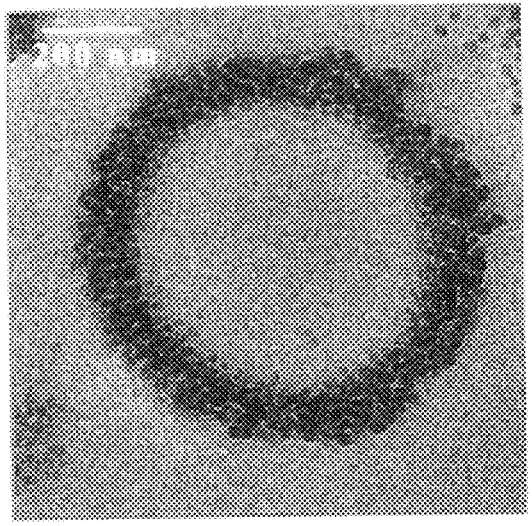

FIGS. 4 and 5 compare $SiO_2$/PDADMAC multilayer coated latex particles having different shell thicknesses before and after core removal. FIG. 6 is a magnified picture of a hollow shell. It can be gathered from these results that intact hollow shells may be obtained which have sufficient permeability for the contents of the decomposed core to be expelled. FIG. 7 shows an image of a broken sphere wall taken by atomic force microscopy (AFM), showing the wall is comprised of silica nanoparticles. The TEM micrograph of hollow silica spheres produced by calcination of PS latices coated with two $SiO_2$/PDADMAC in FIG. 8 shows the uniformity of the wall thickness. Upon careful examination two layers of silica nanoparticles can be observed. The uniformity of the shell wall thickness can also be seen from the TEM micrograph of resin-embedded silica hollow capsules as shown in FIG. 9. The similar contrast both inside and outside the hollow spheres indicates that the spheres are permeable to the resin.

EXAMPLE 2

Figure 10:
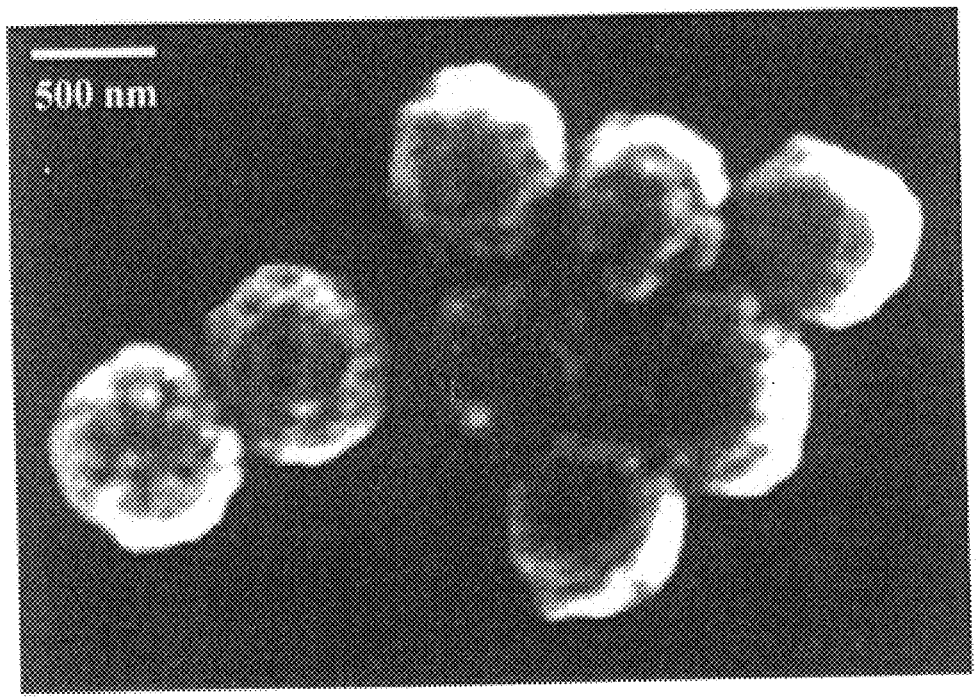
FIG. 10 shows an SEM image of hollow magnetite spheres. These hollow magnetic spheres are formed by depositing four layers of magnetite ($Fe_3O_4$) nanoparticles in alternation with PDADMAC on 640 nm PS latices and then calcining the sample.

According to the procedure described in Example 1 alternating $Fe_3O_4$-PDADMAC multilayers were deposited on 640 nm PS latex particles. After calcining the sample hollow magnetic spheres were formed. An SEM image of these spheres is shown in FIG. 10.

EXAMPLE 3

Figure 11:
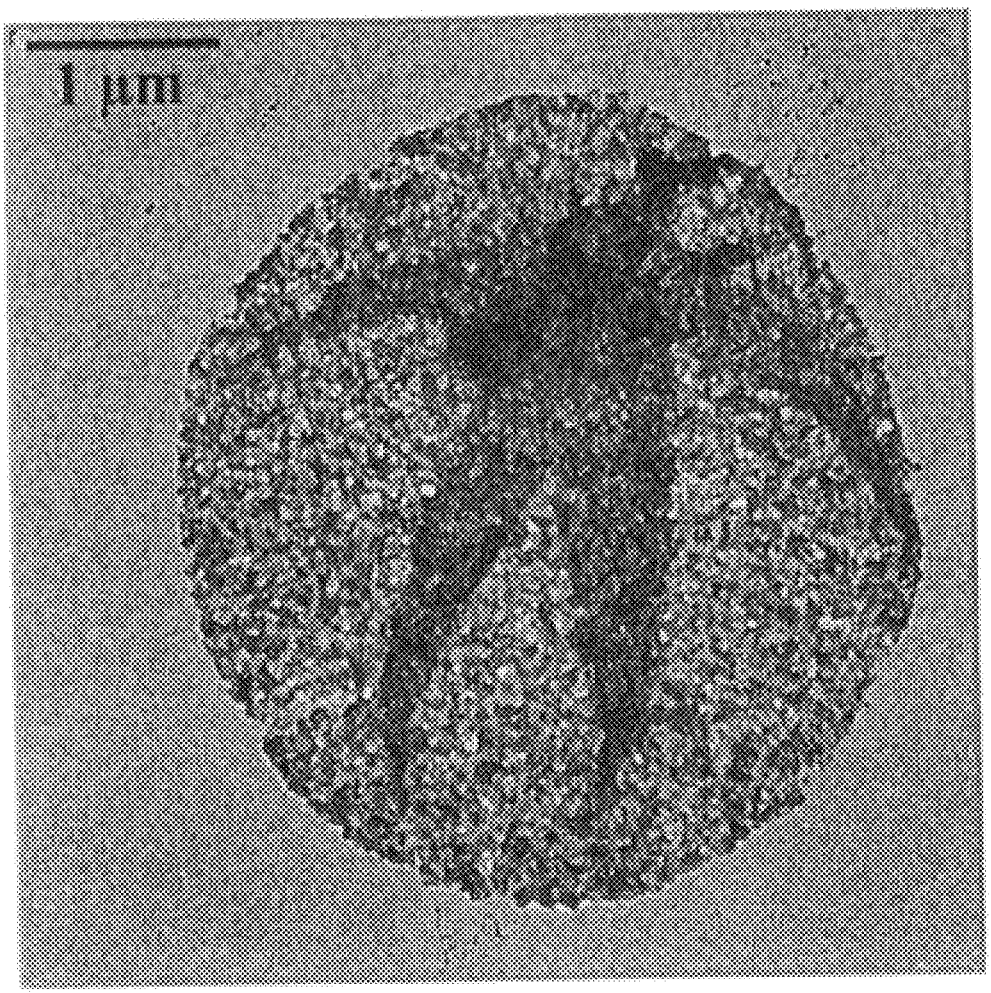
FIG. 11 shows a TEM micrograph of a 3 $\mu$m melamine-formaldehyde particle coated with three $SiO_2$/PDADMAC layer pairs followed by exposure to a solution of pH=1.

According to the procedure described in Example 1 alternating $SiO_2$-PDADMAC multilayers were deposited on 3 μm partially cross-linked melamine formaldehyde particles as described in DE 198 12 083.4. The melamine formaldehyde particles were dissolved by exposure to a solution of pH=1. A TEM micrograph of a resulting hollow particle is shown in FIG. 11. The diameter of the hollow composite sphere is significantly larger than the size of the MF colloid template due to drying of the sample on a solid substrate. The rough surface texture is due to the presence of $SiO_2$ nanoparticles embedded between polymer layers.

EXAMPLE 4

Alternating protein-polyelectrolyte multilayers were deposited on colloid particles.

4.1 Materials

Fluorescein isothiocyanate-labelled bovine serum albumin (FITC-BSA) and sheep immunoglobulin G (IgG) were obtained from Sigma. Poly(allylamine hydrochloride) (PAH), $M_w$ 8,000–1,000 or 50,000–65,000, poly (diallyldimethyl-ammonium chloride) (PDADMAC), $M_w$<200,000, and poly(sodium 4-styrenesulfonate) (PSS), $M_w$ 70,000, were purchased from Aldrich. All proteins and polyelectrolytes were used as received, except for the 70,000 $M_w$ PSS which was dialyzed against water ($M_w$ cut-off 14,000) and lyophilized before use. The negatively charged sulfate-stabilized polystyrene (PS) latex particles (diameter 640 nm) were prepared as described in Example 1.

4.2 Assembly of Protein Multilayers onto Colloids

Precursor polyelectrolyte multilayer films consisting of PAH and PSS or PDADMAC and PSS were first deposited in order to provide a uniformily charged surface and to facilitate subsequent protein adsorption. The precursor films were formed as described in Example 1.

Protein multilayers were fabricated by exposure of the polyelectrolyte-coated PS latex particles to protein solution under conditions where the protein and particles bear opposite charges, followed by alternate adsorptions of polyelectrolyte and protein. FITC-BSA was deposited onto (PDADMAC/PSS/PDADMAC)-precoated PS latex particles, and IgG onto (PAH/PSS)$_2$-precoated particles. The particles have a positive surface charge when PAH or PDADMAC form the outermost layers, and a negative charge when PSS is the outermost layer. FITC-BSA multilayers were formed by the alternate adsorption of FITC-BSA (0.5 mg/ml in PBS buffer at pH 7.0, 30 min adsorption, or 1 mg/ml in water at pH≈5.6, 20 min adsorption) and PDADMAC (1 mg ml/0.5 M NaCl, 20 min) onto the coated PS latex particles (5×10$^9$ particles). IgG multilayers were prepared by successive adsorptions of IgG (1 mg/ml in 0.05 M 2-(N-morpholino) ethanesulfonic acid (MES) buffer at pH 6.0 pH adjusted using NaOH, 45 min adsorption) and PSS ($M_w$ 8,000–11,000, 1 mg/ml/0.5 M NaCl, 20 min) layers onto the coated PS latex particles (6×10$^9$ particles). (In all cases the concentration of the protein is approximately ten times that required for saturation adsorption of the particle surface). After each deposition of protein or polyelectrolyte layer, the samples were centrifuged at ca. 5000×g for 10 min, the supernatant removed, and at least three water washings performed.

4.3 Electrophoretic Mobility (EPM) Measurements

Electrophoretic mobilities of the bare and coated PS latex particles were measured using a Malvern Zetasizer 4 as described in Example 1. All Zeta-potential measurements were performed on coated PS latex particles re-dispersed in air-equilibrated pure water (pH≈5.6).

4.4 Single Particle Light Scattering (SPLS) Experiments

Details of the SPLS experimental system and measurement principle were as described in Example 1. Briefly, the dispersion (of either uncoated or coated PS latex particles) is passed through a capillary with a 0.1 mm diameter orifice at the end. Hydrodynamic focussing is applied so that the dispersion stream is directed through a laser beam which is focussed to allow only a single particle or aggregate in focus at a particular time. This requires particle concentrations of less than 3×10$^8$ particles ml$^{-1}$. The light scattered by the particles moving through the laser focus is recorded in the angular region of 5–10° in the forward direction. The intensity distributions, obtained with a resolution of 0.5%, are collected by a multi-channel analyser and then stored on a PC.

4.5 Transmission Electron Microscopy (TEM)

TEM measurements were performed on a Philips CM12 microscope operating at 120 kV. Samples for TEM were prepared by deposition of aqueous solutions of the coated PS latex particles upon a carbon-coated copper grid. The mixtures were allowed to air dry for one minute and the extra solution was then blotted-off.

4.6 Steady-state Fluorescence Measurements

Fluorescence spectra were recorded using a Spex Fluorolog 1680 spectrometer with excitation and emission bandwidths set at 1.0 nm. Typically, ca. 50–100 µl of the protein multilayer-coated PS latex suspension (ca. 10$^9$ particles ml$^{-1}$) was pipetted into 3 ml of water in a fluorimeter cell and the dispersion agitated for 0.5 min. The fluorescence spectrum of this dispersion was then recorded.

4.7 Results

The assembly of protein multilayers was first followed by EPM measurements. Prior to the formation of protein multilayers, a precursor three or four layer polyelectrolyte multilayer film was deposited onto the PS latex particles. The precursor film not only provides a uniformily charged surface, which facilitates subsequent protein adsorption, but it also allows the surface charge to be altered (depending on whether the polycation or polyanion forms the outermost layer) so that the protein can be deposited under conditions where it is oppositely charged to the adsorbing surface.

A three layer (PDADMAC/PSS/PDADMAC) film was assembled onto the negatively charged PS latices prior to deposition of FITC-BSA, whilst a four layer (PDADMAC/PSS)$_2$ film was deposited onto the particles before IgG adsorption. The negatively charged (uncoated) PS latex particles have a Zeta-potential of about −65 mV in water. The Zeta-potential of the PDADMAC/PSS/PDADMAC-coated particles is ca. +50 mV, in accordance with the outermost layer being a polycation. For the (PDADMAC/PSS)$_2$-coated PS latex particles, the Zeta-potential is ca. −40 mV, consistent with the outermost layer being the polyanion PSS. FIG. 12 shows the Zeta-potential as a function of layer number for the polyelectrolyte-modified PS latex coated with FITC-BSA/PDADMAC or IgG/PSS multilayers. The alternate assembly of FITC-BSA and PDADMAC causes a reversal in sign of the Zeta-potential with each deposition up to 10 layers. When FITC-BSA forms the outermost layer, the Zeta-potential of the coated particles is slightly negative (−10 to −20 mV). Subsequent adsorptions of PDADMAC and FITC-BSA produce positive and negative Zeta-potentials, respectively. For the IgG/PSS multilayer system, Zeta-potential values close to 0 or slightly negative are observed when IgG is the outermost layer. Thus, a reversal of surface charge is not required in the build-up of monoparticle/monoelectrolyte multilayers, e.g. IgG/PSS.

EPM measurements where the Zeta-potential was recorded as a function of pH were conducted on (PAH/PSS)$_2$-modified PS latex particles coated with one IgG layer (FIG. 13). The results show an isoelectric point of approximately 5.5.

Further evidence for the growth of FITC-BSA/PDADMAC multilayers was provided by fluorescent measurements. The fluorescence spectra for FITC-BSA/PDADMAC multilayers, for the cases where FITC-BSA or PDADMAC form the outermost layer, are shown in FIG. 14. The emission maximum occurs at 515 nm when the outer layer is FITC-BSA. When PDADMAC is the outer layer, this maximum red-shifts by about 6–7 nm to 521–522 nm. Reproducible, oscillating maxima were observed for each deposition of FITC-BSA and PDADMAC.

In order to obtain quantitative evidence of step-wise protein multilayer growth, the technique of SPLS was employed. SPLS is a sensitive optical technique which enables determination of the thickness of layers assembled onto colloids, as well as the state and degree of the coated colloids with respect to aggregation. By passing a dispersion of the coated particles through a capillary and hydrodynamically focusing the dispersion, the light scattered from one particle at a given moment in time is recorded. Repeating this process allows a histogram of particle number versus scattering intensity to be obtained. FIG. 15 shows the normalized SPLS intensity distributions for (PDADMAC/PSS/PDADMAC)-modified PS latex particles (a), and the same particles coated with one (b) and three (c) FITC-BSA/PDADMAC multilayers. There is a systematic shift in the SPLS intensity distribution (in the x-axis direction) with increasing multilayer layer number, confirming the growth of FITC-BSA/PDADMAC multilayers on PS latex particles. Similar SPLS intensity distributions were obtained for the IgG/PSS multilayers on PS particles. The peaks seen in the SPLS curves shown in FIG. 15 correspond to singlets, i.e. unaggregated protein multilayer-coated particles. Analysis of the data revealed that the coated particles exist predominantly as singlets, with less than 20% of the particles as doublets (an aggregate of two particles). The fraction of doublets was considerably reduced (<5%) when the polyelectrolyte was outermost layer. This indicates that adsorption of the polyelectrolyte separates some of the weakly and reversibly flocculated protein multilayer-coated particles.

By using the Rayleigh-Debye-Gans theory, and refractive indices (n) of 1.43 and 1.47 for the protein and polyelectrolyte layers, respectively, the average thickness of the protein/polyelectrolyte multilayers on the PS latex particles (d) can be determined. For the FITC-BSA multilayers, the layer thickness increases linearly with the number of protein layers deposited (FIG. 16). The calculated average layer thickness increment for the FITC-BSA layers is 3.3±1.1 nm when FITC-BSA is adsorbed from pure water, and 5.8±2.5 nm when adsorbed from PBS. The difference in thickness is attributed to the different conditions under which the protein was deposited. These data clearly show that BSA multilayers can be grown by the step-wise adsorption of protein and PDADMAC onto PS latex particles.

FIG. 17 shows the layer thickness of IgG/PSS multilayers assembled on (PAH/PSS)$_2$-coated PS latex particles as a function of layer number. Regular, step-wise multilayer growth is observed. The IgG multilayer film growth is linear after the first deposition step, as shown in FIG. 18. The thickness of the first IgG layer deposited is approximately 11 nm. The IgG average thickness increment after the first deposition cycle (of IgG and PSS) is 37±7 nm.

Direct visualization of the protein multilayer growth process is provided by TEM. FIG. 19 shows the TEM micrographs of PDADMAC/PSS/PDADMAC-modified PS latex particles (a and c) and the same particles coated with (FITC-BSA/PDADMAC)$_2$/FITC-BSA multilayers (b and d). The polyelectrolyte-coated PS latex particles closely resemble uncoated PS latices in appearance: they exhibit a smooth surface. The thickness of the polyelectrolyte coating (PDADMAC/PSS/PDADMAC) is approximately 3–4 nm (from SPLS experiments). The presence of FITC-BSA multilayers on the PS latices produces both an increase in surface roughness and an increase in the diameter of the polyelectrolyte-coated PS latices (b and d). The increase in surface roughness is most notable at higher magnification (compare images a and d). The diameter increase of the particles with (FITC-BSA/PDADMAC)$_2$/FITC-BSA layers is approximately 20 nm, corresponding to a layer thickness increase of about 10 nm. This value is in close agreement with the SPLS thickness for the same multilayer (11 nm). The TEM images for FITC-BSA multilayer-coated PS latex particles confirm that a uniform coating of the particles is obtained with deposition of FITC-BSA multilayers (FIG. 19b and 19d).

The TEM micrographs for the IgG/PSS multilayer-coated PS latex particles (FIG. 20) clearly demonstrate a regular layering of the particle surface by the protein multilayers. The diameter of the IgG multilayer particles is significantly larger than those onto which the multilayers were formed. The deposition of one, three and five IgG layers resulted in an increase in diameter of approximately 16, 164 and 296 nm, respectively. These values correspond to layer thickness increases of 8, 82 and 148 nm, and are in excellent agreement with those calculated from SPLS measurements (11, 90 and 160 nm for 1, 3 and 5 IgG layers, respectively).

EXAMPLE 5

PS latex particles (640 nm in diameter) were used as substrate for the adsorption of polyelectrolyte and enzyme layers. The layering procedure started with the adsorption of four alternating PAH (Mw 50–65 kD) and PSS (Mw about 70 kD) layers onto the PS latex resulting in negatively charged particles with PSS at the outermost coating. Polyelectrolytes were allowed to adsorb within 20 min. Each layering step was followed by four washing cycles with deionized water. After every layering and washing step the mixtures were centrifuged at 7000 rpm for 8 min and the supernatants were removed. Onto the last PSS layer βglucosidase from Caldocellum saccharolyticum obtained from Sigma (EC 3.2.1.21) was adsorbed in one hour. The enzyme was used as 1.4 mg/ml solution in 0.1 M acetate buffer pH=4.8. The described procedure was repeated until four enzyme layers each separated by one PSS layer were assembled on the particles. Samples were taken after each layering step yielding samples with 1 to 4 enzyme layers having either enzyme or PSS as the outermost coating. These samples were used as catalysts in enzymatic glucosidations.

Glucosidations were carried out in 2 ml tubes which were shaken (200 min$^{-1}$) at 40° C. Enzyme modified latex particles were suspended in 100 μl phosphate buffer pH=6.8 solution. In a typical experiment 413 mg (2.22 mmoles) n-dodecanol (Fluka), 600 μl acetonitrile (Merck), and 100 mg (0.55 mmoles) anhydrous glucose (Merck) were added. The mixtures were shaken thoroughly to homogenize and then kept at 40° C. for 72 hours with shaking. The mixtures were then centrifuged at 5000 rpm for 10 min. The supernatants were removed and the remainders were washed with 500 μl acetonitrile. From the combined organic phases of each sample the solvent was distilled off. The concentrated crude products were subjected to a preparative chromatographic separation to remove excess dodecanol.

Preparative liquid chromatography was done with a Büchi-680 HPLC equipment consisting of chromatography pump, gradient former, fraction collector, and a Knauer polar monitor detector. The column was a Kronlab bio-cart (20 mm×120 mm) packed with 10 g of 15 μm spherical silica. By collecting 10 ml fractions with an ethyl acetate/methanol gradient program (0 to 100% methanol, 34 min) all excess dodecanol could be separated from the crude product. The remaining fractions were combined, concentrated and then fixed to a volume of 1 ml by adding a water/propane-2-ol (1:33 v/v) mixture. To determine the amount of formed dodecyl glucoside aliquots of these stock solutions were analyzed by HPLC on a JASCO chromatograph equipped with a light scattering detector and silica column. For the quantitative determination of dodecyl glucoside calibration curves were constructed.

In the case of particles having enzyme or PSS as outermost layers dodecyl glucoside could be detected. Thus, the enzyme is not inactivated by the coating procedure. In the case of particles having PSS as the outermost layer an increasing yield of dodecyl glucoside with increasing numbers of deposited enzyme layers on the particles was observed. This shows that also layers underneath take part in the catalytic process.

What is claimed is:

1. A process for preparing coated particles comprising the steps:

(a) providing template particles and (b) coating said template particles with a multilayer comprising (i) alternating layers of oppositely charged nanoparticles and polyelectrolytes and/or (ii) alternating layers of oppositely charged nanoparticles.

2. The process of claim 1 wherein said template particles have an average diameter of 10 μm or less.

3. The process of claim 1, wherein said template particles are at least one member selected from the group consisting of organic particles and inorganic particles.

4. The process of claim 1 wherein said template particles are selected from organic polymer latices and partially cross-linked melamine-formaldehyde particles.

5. The process of claim 1 wherein the polyelectrolyte is a linear molecule.

6. The process of claim 1, wherein the polyelectrolyte is a polycation and the nanoparticle has an overall anionic charge.

7. The process of claim 1, wherein the polyelectrolyte is a polyanion and the nanoparticle has an overall cationic charge.

8. The process of claim 1, wherein said nanoparticles have an average diameter of from 1 to 100 nanometers.

9. The process of claim 1, wherein said nanoparticles are inorganic particles.

10. The process of claim 9, wherein said nanoparticles are selected from ceramic and metal particles.

11. The process of claim 10, wherein said nanoparticles are silicon dioxide particles.

12. The process of claim 1, wherein said nanoparticles are biomolecules.

13. The process of claim 12, wherein said biomolecules are polypeptides.

14. The process of claim 1, further comprising the step of at least partially disintegrating the template particles.

15. The process of claim 14, wherein said disintegration is carried out by thermal treatment, chemical treatment or pH adjustment.

16. A coated particle having a core which is a template particle and a multilayer shell comprising a member selected from the group consisting of alternating layers of (i) oppositely charged nanoparticles and polyelectrolytes, and (ii) oppositely charged nanoparticles.

17. The particle of claim 16 having an average diameter of less than or equal to 15 microns.

18. A hollow shell obtained by disintegrating the template particle of the coated particle of claim 16.

19. The hollow shell of claim 18 which is an inorganic structure.

20. The hollow shell of claim 16 which is an organic structure.

21. The hollow shell of claim 16 which is a composite organic-inorganic structure.

22. The hollow shell of claim 16 which is a composite inorganic-inorganic structure.

23. The shell of claim 16 containing an active agent.

24. The hollow shell of claim 23, wherein said active agent is selected fromthe group consisting of pharmaceuticals, contrasting agents, herbicides, pesticides, catalysts and pigments.

25. The shell of claim 23, wherein the shell provides sustained release of said active agent.

26. The shell of claim 23, wherein said shell provides targeted release of said active substance.

* * * * *